United States Patent [19]

Nakai et al.

[11] Patent Number: 4,845,210
[45] Date of Patent: Jul. 4, 1989

[54] AZETIDINONE DERIVATIVES AND PROCESSES FOR PRODUCTION THEREOF

[75] Inventors: Takeshi Nakai, Yokohama; Toshiyuki Chiba, Osaka, both of Japan

[73] Assignee: Fujisawa Pharmaceutical Co., Ltd., Osaka, Japan

[21] Appl. No.: 168,532

[22] Filed: Mar. 8, 1988

Related U.S. Application Data

[63] Continuation of Ser. No. 762,830, Aug. 6, 1985, abandoned.

[30] Foreign Application Priority Data

Aug. 6, 1984 [GB] United Kingdom ............... 8419962
Oct. 29, 1984 [GB] United Kingdom ............... 8427260
Mar. 7, 1985 [GB] United Kingdom ............... 8505926
Jun. 20, 1985 [GB] United Kingdom ............... 8515687

[51] Int. Cl.$^4$ .................. C07D 205/08; C07B 55/00; C07F 7/18; C07F 7/10
[52] U.S. Cl. ................................ 540/200; 540/357
[58] Field of Search ....................... 540/200

[56] References Cited

FOREIGN PATENT DOCUMENTS 0082133  6/1983  European Pat. Off. .
0091239 10/1983  European Pat. Off. .
0101598  2/1984  European Pat. Off. .
0106652  4/1984  European Pat. Off. .
0126709 11/1984  European Pat. Off. .
3215103 11/1982  Fed. Rep. of Germany .
3336262  4/1984  Fed. Rep. of Germany .

OTHER PUBLICATIONS

Chiba et al., Tet. Letters 26, 4647 (1985).
Yang, PHD Thesis, Ohio State U. (1983), p. 160, 166–167, 212–213, 227–231.
Chiba et al., Chemistry Letters, 1984, 1927 (Nov. 84).
Ha et al., J. Amer. Chem. Soc. 1984, 4819 (Aug 22, 1984 issue).
Hart, J. Org. Chem., 48, 289 (1983).
Colvin et al., J. Chem. Soc. Chem. Comm. (May 1, 1985).
Kobayashi, J.C.S. Chem. Comm. 1980, p. 736–777 (1980).
Cimarusti, Tetraherdron 39, 2577 (1983).

Primary Examiner—Mark L. Berch
Attorney, Agent, or Firm—Oblon, Spivak, McClelland, Maier & Neustadt

[57]  ABSTRACT

The invention relates to a method of producing an azetidinone derivative of the formula:

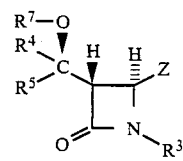

which comprises reacting a compound of the formula

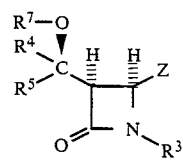

with a compound of the formula

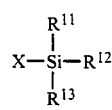

and then subjecting the resulting compound to hydrolysis, the substituents above being as defined in the specification.

1 Claim, No Drawings

AZETIDINONE DERIVATIVES AND PROCESSES FOR PRODUCTION THEREOF

This application is a division of application Ser. No. 762,030, filed on Aug. 6, 1985, now abandoned.

This invention relates to azetidinone derivatives and processes for production thereof.

One object of this invention is to provide a new azetidinone derivative of the formula (I) given below, which is of use as an intermediate for the production of carbapenem compounds having potent antimicrobial activity and high β-lactamase-inhibitory activity such as thienamycin and carpetimycin.

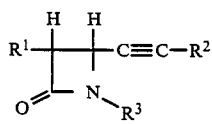

wherein $R^1$ is a hydrogen or an organic residue,
$R^2$ is a hydrogen or a protective group, and
$R^3$ is a hydrogen or a protective group.

Another object of this invention is to provide optically active azetidinone derivatives (Ia), (Ib), (Ic) and (Id).

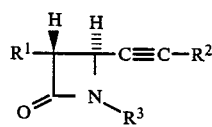

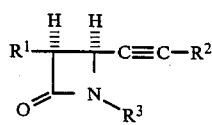

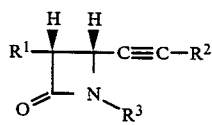

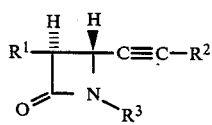

wherein $R^1$, $R^2$ and $R^3$ are each as defined above,
⦀ is an alpha configuration bond, and
► is a beta configuration bond.

Further object of this invention is to provide a method for preparing 4-acetoxy-2-azetidinone (Va) which is known as a key intermediate for the synthesis of Thienamycin and other carbapenem compounds.

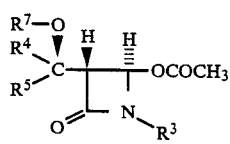

wherein $R^3$ is as defined above, $R^4$ and $R^5$, which may be the same or different, are hydrogen or lower alkyl group and $R^7$ is a hydrogen or a protective group.

Heretofore, although several attempts have been made to provide 3-(1-hydroxyethyl)-4-acetoxy-2-azetidinone (A), there remains yet to be established a process for producing it practically in high yield.

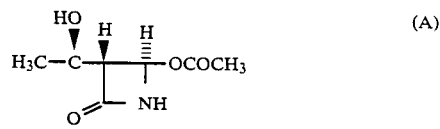

For example, according to Tetrahedron Letters, Vol. 23, pp. 2293 to 2296 (1982), (3R,4R)-3-[(R)-1-hydroxyethyl]-4-acetoxy-2-azetidinone was obtained from L-aspartic acid in 21% yield by 7 steps or more. Further, according to Tetrahedron Vol. 39, pp 2505 to 2513 (1983), (3R,4R)-3-[(R)-1-(t-butyldimethylsilyloxy)ethyl]-4-acetoxy-2-azetidinone was obtained from 6-aminopenicillanic acid in 17% yield by 7 steps or more.

The research undertaken by the present inventors for the development of a method for producing the above compound (A) in good yields resulted in the finding that the novel 4-ethynyl-2-azetidinone derivative of the above general formula (I) is a useful intermediate for the production of such compounds and that this intermediate can be produced in good yield by the processes herein disclosed.

According to this invention, 4-acetoxy-2-azetidinone derivative (V) including 3-(1-hydroxy)-4-acetoxy-2-azetidinone (A) can be obtained from a reactive derivative of alkanoic acid alkyl ester (II) and ethynylaldimine (III) by 3 steps via a new 4-ethynyl-2-azetidinone derivative (I).

Namely, this invention can be illustrated in the following schema 1.

Schema 1 reactive derivative of
$R^1$—$CH_2$—$COOR^{10}$ + $R^2$—C≡C—CH=N—$R^3$ (II)                          (III)

↓ Process 1

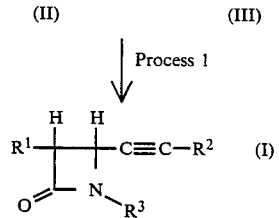

↓ Process 2

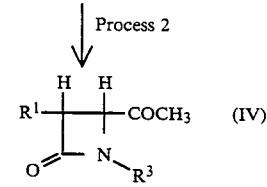

↓ Process 3

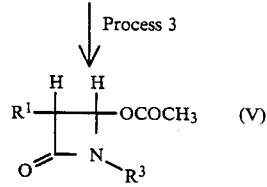

wherein $R^1$, $R^2$ and $R^3$ are each as defined above, and $R^{10}$ is a lower alkyl group.

PROCESS 1

4-Ethynyl+-2-azetidinone derivative (I) (hereinafter, in this specification, any group which may optionally be protected by a protective group will be designated by a mark, plus +) can be prepared by reacting a reactive derivative of alkanoic acid alkyl ester (II) with an ethynylaldimine (III).

Ethynylaldimine (III) can be produced by reacting an ethynyl+carbaldehyde (III) ($R^2$—C≡C—CHO) with a lithium bis(trimethylsilyl)amide in a solvent such as an ether (e.g. tetrahydrofuran, diethyl ether, dimethyl ether, etc.) or the like at a temperature below −65° C. The lithium bis(trimethylsilyl)amide is obtainable by reacting 1,1,1,3,3,3-hexamethyldisilazane with butyllithium in the above etheral solvent at a temperature below 15° C., preferably below 0° C.

Suitable example of reactive derivative of alkanoic acid alkyl ester (II) is lithium enolate compound of the alkanoic acid alkyl ester. The lithium enolate compound can be prepared by reacting the ester with lithium diisopropylamine or lithium bis(trimethylsilyl)amide which can be obtainable as above.

The reaction of the reactive derivative of alkanoic acid alkyl ester (II) and the ethynylaldimine (III) can be conducted in an etheral solvent as exemplified before at a temperature not exceeding −50° C. optionally in an atmosphere of argon gas or nitrogen gas. The object compound (I) can be isolated in a conventional manner.

The object compound (I) can optionally be subjected to an introduction reaction of a protective group followed by the Process 2.

PROCESS 2

4-Acetyl-2-azetidinone derivative (IV) can be obtained by treating a 4-ethynyl+-2-azetidinone (I) with a mercuric compound, for example, mercuric sulfate in the presence of concentrated sulfuric acid, and/or ammonium sulfate, preferably in polar solvent such as alcohol (e.g. methanol, ethanol, etc.), etheral solvent as exemplified before, water and a mixture thereof at a temperature between room temperature and about 100° C.

The object compound (IV) can be subjected to Process 3 after isolation or without isolation.

PROCESS 3

4-Acetoxy-3-azetidinone derivative (V) can be obtained by subjecting 4-acetyl-2-azetidinone derivative (IV) to a so-called Baeyer-Villiger reaction or a chemical equivalent thereof.

This reaction is conducted in a conventional manner, for example, by treating the compound (IV) with a peracid such as metachloroperbenzoic acid in an inert solvent such as chloroform, carbon tetrachloride, methylene chloride, ethyl acetate, etc. at room temperature or under mild heating.

The object compound (V) can optionally be isolated from the reaction mixture after treating the reaction mixture with a reducing agent such as dimethyl sulfide.

The suitable exemplifications of each definition in this specification are as follows.

The term "lower" is intended to mean 1 to 6 carbon atoms.

The "lower alkyl group" is a straight-chain or branched-chain alkyl group of 1 to 6 carbon atoms, such as methyl, ethyl, propyl, isopropyl, butyl, isobutyl, sec-butyl, tert-butyl, pentyl and hexyl.

The "organic residue" for $R^1$ is a residue derived from an organic compound by removal of one hydrogen atom. Such organic residue includes, for example, alkyl, alkoxy, alkanoyl, cycloalkyl, alkenyl, alkynyl, cycloalkenyl, aryl and the like, which may optionally be substituted with one to three substituents.

The alkyl is preferably a straight or branched lower alkyl as exemplified above.

Suitable examples of such substituent on alkyl group are halogen, oxo group, hydroxy group, protected hydroxy group, alkoxy group, sulfo group, aryloxy group, carbamoyloxy group, alkanesulfonyloxy group, arylsulfonyloxy group, aryl group, alkoxycarbonyl group, nitro group, tri(lower) alkyl)silyl group, amino group and the like.

"Halogen" include chlorine, bromine, iodine and fluorine.

Suitable "protected hydroxy" is a hydroxy group which is protected with a conventional protective group. Such protective group on the hydroxy group is a group which has been commonly used as a hydroxy-protecting group in organic chemistry and particularly in the field of β-lactam chemistry. Thus, for example, optionally substituted alkanoyl groups such as formyl, acetyl, propionyl, butyryl, valeryl, pivaloyl, chloroacetyl, etc., esterified carboxy groups such as β,β,β-trichloroethoxycarbonyl, β-trimethylsilylethoxycarbonyl, etc., optionally substituted alkyl groups such as tert-butyl, benzyl, p-nitrobenzyl, trityl, β-methoxyethoxymethyl, etc., silyl residues such as trimethylsilyl, tert-butyldimethylsilyl, etc., boron residues such as diborane residue, triisopropyl borate residue, etc., acetal residues such as 2-tetrahydropyranyl, 4-methoxy-4-tetrahydropyranyl, etc., aroyl groups such as benzoyl, p-toluoyl, m-toluoyl, naphthoyl and the like may be exemplified.

Suitable examples of "alkoxy group" are methoxy, ethoxy, propoxy, isopropyloxy, butoxy, t-butoxy, pentyloxy, hexyloxy and the like.

Suitable examples of "aryl group" are phenyl, tolyl, xylyl, naphthyl, biphenylyl and the like.

Suitable examples of the aryl group of "aryloxy and arylsulfonyloxy" are the same as exemplified above.

Suitable examples of "alkanesulfonyloxy group" are mesyloxy, ethanesulfonyloxy, isopropanesulfonyloxy and the like.

Suitable examples of "alkoxycarbonyl group" are methoxycarbonyl, ethoxycarbonyl, isopropyloxycarbonyl and the like.

More preferable example of the "alkyl group" optionally substituted with one to three substituents as exemplified before is a group

wherein $R^4$ and $R^5$, which may be the same or different, are hydrogen or lower alkyl group, and $R^6$ is a hydrogen, halogen, hydroxy or protected hydroxy group, or $R^5$ and $R^6$ are taken together to represent an oxo group.

The alkanoyl includes, for example, those having 1 to 6 carbon atoms such as formyl, acetyl, propionyl, valeryl, pivaloyl, hexanoyl or the like.

The cycloalkyl preferably has 3 to 12 carbon atoms and includes, for example, cyclopropyl, cyclobutyl, cyclopentyl, adamantyl, or the like.

The alkenyl is preferably a straight or branched chain lower alkenyl having 2 to 6 carbon atoms such as vinyl, allyl, isopropenyl, 2-butenyl or the like.

The alkynyl is preferably a straight or branched chain lower alkynyl having 2 to 6 carbon atoms such as ethynyl, 1-propynyl, 2-propynyl, 3-butynyl, 4-pentynyl or the like.

The cycloalkenyl includes, for example, those having 3 to 8 carbon atoms such as 1-cyclopropenyl, 2-cyclobutenyl, 1-cyclopentenyl and the like.

The above "alkoxy group, alkanoyl group, cycloalkyl group, alkenyl group, alkynyl group, cycloalkenyl group and aryl group" for an organic residue of $R^1$, may also be substituted with one to three substituents as exemplified before for the alkyl group.

Suitable example of a protective group for $R^2$ is an optionally substituted tri(lower alkyl)silyl group, wherein the three lower alkyl groups, which may be the same or different, are the above exemplified lower alkyl groups. More preferable examples of the protective group for $R^2$ are trimethylsilyl, t-butyldimethylsilyl, isopropyldimethylsilyl, chloromethyldimethylsilyl, and the like.

Suitable example of the protective group for $R^3$ is conveniently selected from those which are conventionally used for protection of amino group in the fields of β-lactam antibiotics. Thus, for example, such amino-protective groups as acyl group (e.g. formyl, acetyl, monochloroacetyl, dichloroacetyl, trichloroacetyl), esterified carboxy group (e.g. tert-butoxycarbonyl, β,β,β-trichloroethoxycarbonyl, β-trimethylsilylethoxycarbonyl, benzyloxycarbonyl, p-nitrobenzyloxycarbonyl, p-methoxybenzyloxycarbonyl), trialkylsilyl group (e.g. trimethylsilyl, tert-butyldimethylsilyl etc.), optionally substituted ar(lower)alkyl group (e.g. benzyl, p-nitrobenzyl etc.) or the like are used. Especially preferable one among these is trialkylsilyl group.

In the foregoing formula (I), the specific preferred examples of those are exemplified below.
3-Ethyl-4-ethynyl-2-azetidinone,
3-ethyl-4-trimethylsilylethynyl-2-azetidinone,
3-(1-hydroxyethyl)-4-ethynyl-2-azetidinone,
3-(1-hydroxyethyl)-4-trimethylsilylethynyl-2-azetidinone,
3-[1-(t-butyldimethylsilyloxy)ethyl]-4-ethynyl-2-azetidinone,
3-[1-(t-butyldimethylsilyloxy)ethyl]-4-trimethylsilylethynyl-2-azetidinone,
3-(1-hydroxy-1-methylethyl)-4-ethynyl-2-azetidinone,
3-(1-hydroxy-1-methylethyl)-4-trimethylsilylethynyl-2-azetidinone,
1-(t-butyldimethylsilyl)-3-(1-hydroxyethyl)-4-ethynyl-2-azetidinone,
1-(t-butyldimethylsilyl)-3-acetyl-4-trimethylsilylethynyl-2-azetidinone,
3-(1-formyloxyethyl)-4-trimethylsilylethynyl-2-azetidinone,
3-(1-benzoyloxyethyl)-4-trimethylsilylethynyl-2-azetidinone, and
3-(1-bromoethyl)-4-trimethylethynyl-2-azetidinone.

The 4-ethynyl-2-azetidinone derivative (I), 4-acetyl-2-azetidinone derivative (IV) and 4-acetoxy-2-azetidinone derivative (V) of this invention can be represented as various stereo isomers (e.g., cis, trans, syn, anti and optically active isomers) and it is understood that the present invention encompasses these isomers as well as mixtures thereof.

More specifically 4-ethynyl-2-azetidinone derivative (I) can be represented as the following individual isomers and/or mixture thereof.

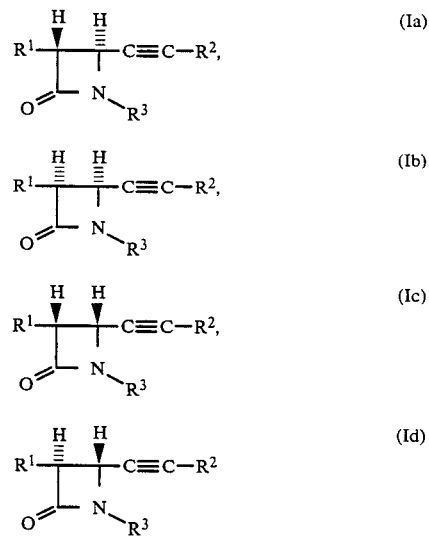

Wherein $R^1$, $R^2$, $R^3$, ⁞⁞⁞⁞ and ► are each as defined above.

In the above formulae, the compounds (Ib) and (Ic) are cis-configuration isomers, and the each isomer and/or mixture thereof can be illustrated below by citing relative configuration bond,

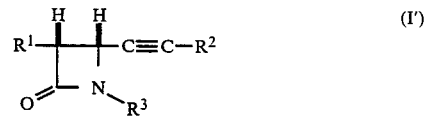

wherein $R^1$, $R^2$ and $R^3$ are each as defined above, and ▬ is a relative configuration bond.

On the other hand, the compounds (Ia) and (Id) are trans-configuration isomers, and the each isomer and/or mixture thereof can be illustrated below,

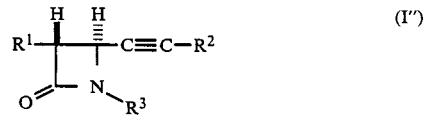

wherein $R^1$, $R^2$, $R^3$, ⋯ and ▬ are each as defined above.

Further, when the $R^1$ of the formulae (Ia to Id) is a group

wherein $R^4$, $R^5$ and $R^7$ are each as defined above,

The following stereoisomers (Ie to Im) can be represented and these isomers can be encompassed in the azetidinone derivatives (I) of this invention.

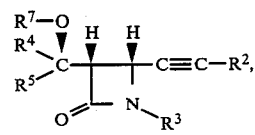 (Ie)

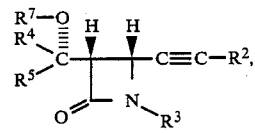 (If)

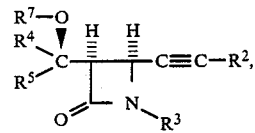 (Ig)

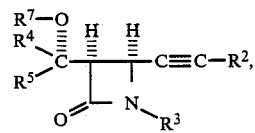 (Ih)

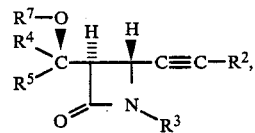 (Ii)

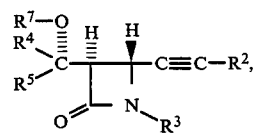 (Ij)

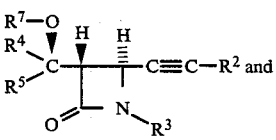 (Ik)

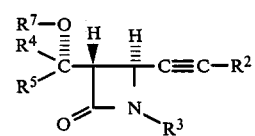 (Im)

wherein $R^2$, $R^3$, $R^4$, $R^5$, $R^7$, and are each as defined above.

Some carbapenem compounds such as Thienamycin and PS-5 having the following formulae are characteristic β-lactam antibiotics exhibiting broad and potent antibiotic activities.

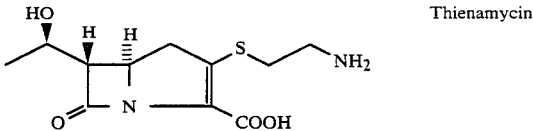 Thienamycin

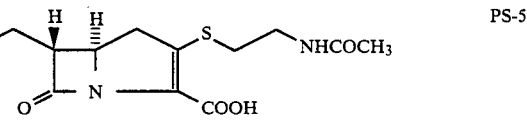 PS-5

However, a fermentation titer of Thienamycin and PS-5 are very low, and therefore, attempts have been made to provide Thienamycin by total synthesis, but there remains yet to be established a process to produce it in good yield. Particularly, the compounds possessing high antimicrobial activity and high β-lactamase-inhibitory activity are natural type of Thienamycin, for example, with the absolute configuration of 5R, 6S, 8R, but there has not been established a technique for total synthesis of such compounds in good yield.

Further, the research undertaken by the present inventors for the development of a stereoselective method for producing compound (A) and (3R,4R)-4-acetoxy-3-[(R)-1-(t-butyldimethylsilyloxy)ethyl]-2-azetidinone (B) in good yield resulted in the finding that the compounds (A) and/or (B) can be produced in good yield by an asymmetric synthesis herein disclosed for this invention.

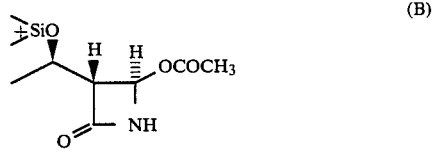 (B)

The stereoselective synthesis for producing the compound (B) of this invention can be illustrated in the following schema 2.

Schema 2 reactive derivatives of

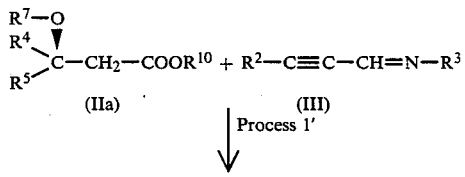

Schema 2 reactive derivatives of

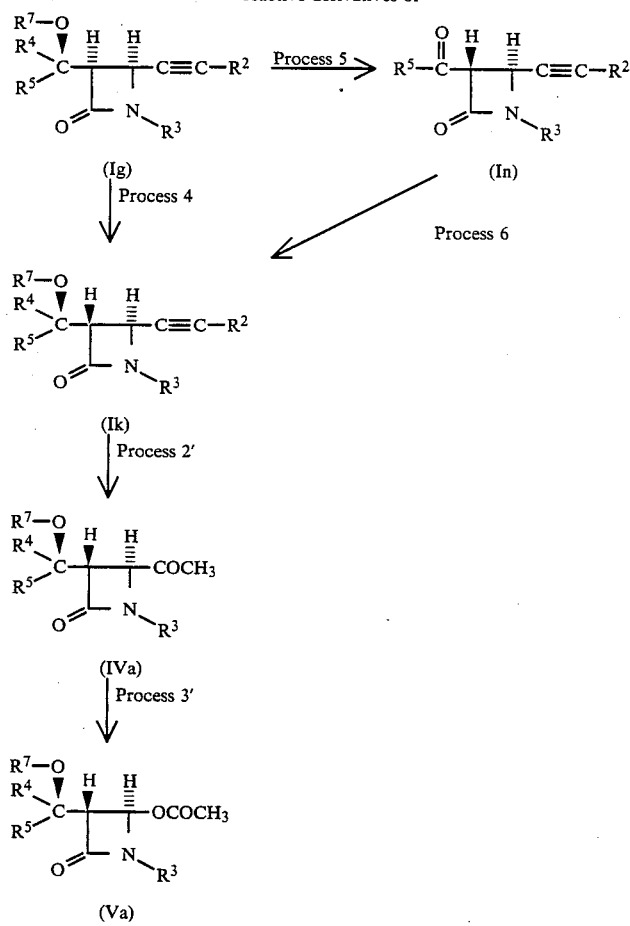

wherein $R^2$, $R^3$, $R^4$, $R^5$, $R^7$, ⦀ and ⇀ are each as defined above.

The reactions depicted above are explained in detail below.

PROCESS 1'

An optical active (R)-β-hydroxyalkanoic acid alkyl ester (IIa) or its protected compound (hereinafter, in this specification, any group which may be optionally be protected by a protective group will be designated by a mark, plus +), namely, (R)-β-hydroxy+alkanoic acid alkyl ester (IIa) is reacted with compound (III) in a similar manner to that of Process 1, instead of alkanoic acid alkyl ester (II) as the starting compound, to give cis-3-[(R)-1-hydroxyalkyl]-4-ethynyl+-2-azetidinone, more specifically, (3R,4S)-3-[(R)-1-hydroxy+alkyl]-4-ethynyl-2-azetidinone (Ig) as a main product.

Some other stereoisomers containing the compounds (Ii) and (Ik) can be produced in a small amount, and these stereoisomers can optionally be isolated by a silica gel column chromatography.

The object compound (Ig) can optionally be subjected to an introduction reaction of a protective group followed by subjecting the Process 4 or 5.

PROCESSES 2' and 3'

The Processes 2' and 3' can be conducted in similar manners to those of the Processes 2 and 3 respectively.

These reactions proceed by retaining the configurations to give the object compounds (IVa and Va) respectively.

An object compound of the Process 3' is trans-3-[(R)-1-hydroxy+alkyl]-4-acetoxy-2-azetidinone, more specifically, (3R,4R)-3-[(R)-1-hydroxy+alkyl]-4-acetoxy-2-azetidinone (Va), which has been reported in Tetrahedron [Vol. 39, No. 15, PP2505 (1983)] as a key-intermediate compound for the synthesis of carbapenem compounds including Thienamycin.

PROCESS 4

Trans-3-[(R)-1-hydroxyalkyl]-4-ethynyl+-2-azetidinone, more specifically, (3S,4S)-3-[(R)-1-hydroxy+alkyl]-4-ethynyl-2-azetidinone (IK) can be prepared by reacting (3R,4S)-3-[(R)-1-hydroxyalkyl]-4-ethyl-2-azetidinone (Ig) with a compound of the formula (VI) (first step)

wherein, $R^{11}$, $R^{12}$ and $R^{13}$, which may be the same or different, are hydrocarbon residue, and X is a strong acid residue, and then by subjecting the resultant to a solvolysis (second step).

Suitable examples of "hydrocarbon residue" are the before-mentioned lower alkyl group, aryl group and the like.

Suitable examples of "strong acid residue" are super acid residue such as trihaloalkanesulfonyloxy (e.g. trifluoromethanesulfonyloxy), trialkylsilyliodide, and the chemical equivalent thereof.

(i) First step

The reaction of a compound of the formula (Ig) with a compound of the formula (VI) can be conducted preferably in a solvent under cooling or warming.

Suitable solvent may be an etheral solvent such as tetrahydrofuran, dimethyl ether, diethyl ether, etc., alcohol such as methanol, ethanol, isopropyl, alcohol, etc., ethyl acetate, halogenated hydrocarbon such as chlorofrom, carbon tetrachloride, methylene chloride, polar solvent such as N,N-dimethylformamide, dimethylsulfoxide or any other solvent which does not adversely affect this reaction.

This reaction can optionally be conducted in the presence of an organic or inorganic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds (e.g. pyridine, picoline, lutidine, N,N-di(lower)alkylaminopyridine such as N,N-dimethylaminopyridine, etc.), quinoline, N-lower alkylmorphorine (e.g. N-methylmorphorine, etc.), N,N-di(lower)alkylbenzylamine (e.g. N,N-dimethylbenzylamine, etc.), and the like, and when the base is liquid, it can be used also as a solvent.

The reaction temperature is not critical, and the reaction is usually carried out from under cooling to under warming, preferably from 0° C. to ambient temperature.

The resultant compound of the above reaction is usually subjected to the following solvolysis without isolation, but optionally may be subjected to the following solvolysis after isolation and purification.

(ii) Second step

The compound obtained by the above step (i) is then solvolyzed in a conventional manner to give a compound of the formula (Ik).

The solvolysis can be conducted in a conventional manner such as hydrolysis, alcoholysis, aminolysis etc.

Among these methods, hydrolysis in the presence of an inorganic or organic acid is one of the preferable method.

Suitable acid to be used in the hydrolysis may include an inorganic acid such as hydrohalogenic acid (e.g. hydrochloric acid, hydrobromic acid, hydriodic acid, etc.), sulfuric acid, boron trihalide (e.g. boron tribromide, boron trichloride, etc.) or the like and an organic acid such as trifluoroacetic acid, para-toluenesulfonic acid, methanesulfonic acid or the like.

The solvolysis can be carried out in a conventional solvent which does not adversely influence the reaction, for example, the one selected from the above exemplified solvents, water and the like or a combination thereof.

The reaction temperature is not critical and the reaction is usually carried out from under cooling to under heating.

According to this Process 4, the configurations at the 3 and 4 positions of an azetidinone ring can easily be transformed into the trans isomer, namely, (3S,4S)-isomer from the cis isomer, and therefore, this Process is very useful for a total synthesis of $\beta$-lactam compound.

On the other hand, when a trans isomer is used as a starting compound, cis isomer can be prepared by this Process.

PROCESS 5

Trans-3-alkanoyl-4-ethynyl+-2-azetidinone, more specifically, (3S,4S)-3-alkanoyl-4-ethynyl+-2-azetidinone (In) can be prepared by oxidizing (3R,4S)-3-[(R)-1-hydroxy+alkyl]-4-ethynyl+-2-azetidinone (Ig).

The oxidation reaction can be conducted by reacting a compound (Ig) with trifluoroacetic anhydride and dimethyl sulfoxide in a solvent such as ether and/or a halogenated hydrocarbon and in the presence of a base such as dimethylamine, diethylamine, triethylamine, etc., or with a metallic oxidizing agent such as manganese dioxide in a solvent such as acetic acid ester, halogenated hydrocarbon, ether, water and the like.

In this reaction, the cis/trans isomerization takes place.

PROCESS 6

Trans-3-[(R)-1-hydroxy+alkyl]-4-ethynyl+-2-azetidinone, more specifically, (3S,4S)-3-[(R)-1-hydroxy+alkyl]-4-ethynyl+-2-azetidinone (Ik) can be prepared by reducing (3S,4S)-3-alkanoyl-4-ethynyl+-2-azetidinone (In).

The reduction can be conducted by using potassium tri-sec-butylborohydride or a chemical equivalent thereof in an etheral solvent at room temperature.

This reaction proceeds stereoselectively to give a (3S,4S)-3[(R)-1-hydroxy+alkyl]-2-azetidinone (Ik).

In the above schema 2, an optical active (S)-$\beta$-hydroxyalkanoic acid alkyl ester (IIb) can be used instead of (R)-$\beta$-hydroxy+alkanoic acid alkyl ester (IIa) as the starting compound and these reactions can be illustrated in the following scheme 3.

Schema 3

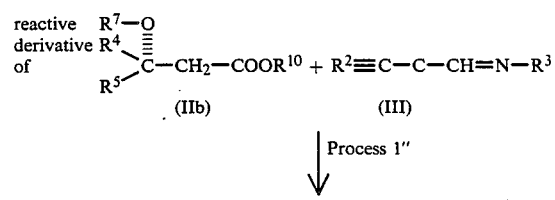

(IIb)   (III)

Process 1''

Schema 3

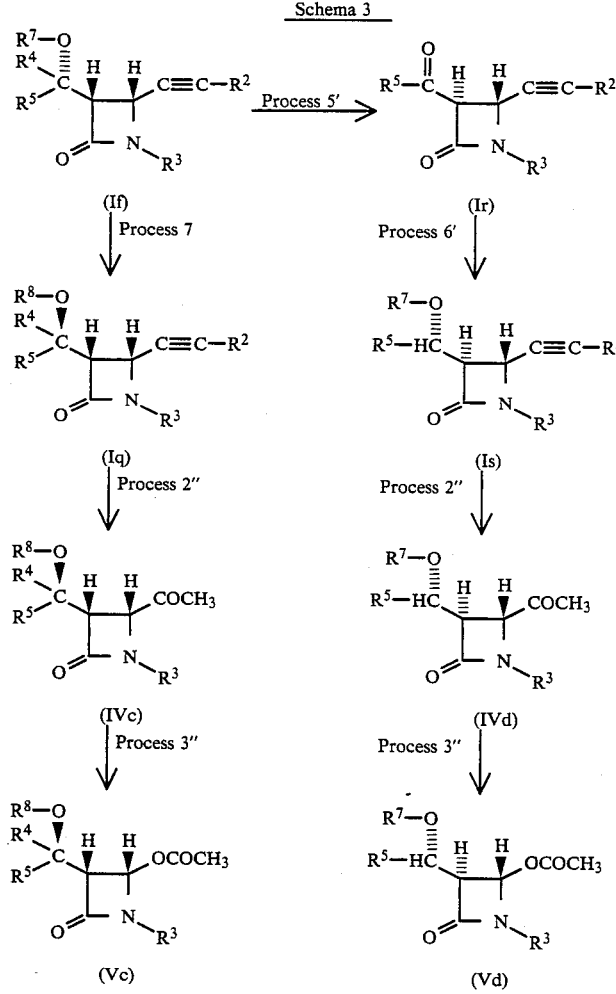

wherein $R^2$, $R^3$, $R^4$, $R^5$, $R^7$, $R^{10}$, and are each as defined above, and $R^8$ is an acyl group.

Suitable examples of "acyl group" are the before-mentioned alkanoyl group, aroyl group, and the like.

The Processes 1", 2", 3", 5' and 6' in the Schema 3 can be conducted in similar manners to those of the Processes 1', 2', 3', 5 and 6 respectively.

Namely (S)-β-hydroxyalkanoic acid alkyl ester (IIb) is reacted with a compound (III) to give (3S,4R)-3-[(S)-1-hydroxy+alkyl]-4-ethynyl+-2-azetidinone (If) selectively, which is then optionally be subjected to an introduction reaction of a protective group followed by Processes 5', 6', 2" and 3" to give compounds (Ir), (Is), (IVd) and (Vd) respectively.

PROCESS 7

(3S,4R)-3-[(R)-1-Acyloxyalkyl]-4-ethynyl-2-azetidinone (Iq) can be prepared by reacting (3S,4R)-3-[(S)-1-hydroxyalkyl]-4-ethynyl-2-azetidinone (If) with a compound of the formula (VII)

$R^8$—OH (VII)

wherein $R^8$ is as defined above, under a condition of a so-called Mitsunobu reaction.

The reaction can be conducted by treating a mixture of the compounds [If] and [VII] with a di(lower alkyl) azodicarboxylate and triphenylphosphine in a conventional solvent as exemplified below at a temperature under cooling to ambient temperature.

The inversion process is usually conducted in a solvent such as acetone, dioxane, tetrahydrofuran, acetonitrile, methylene chloride, pyridine, N,N-dimethylformamide, or the like.

The object compound (Iq) can optionally be subjected to an introduction reaction of a protective group followed by Processes 2" and 3" to give compounds (IVc) and (Vc) respectively.

The 4-ethynyl+-2-azetidinone derivatives (I) of this invention are new and can be prepared by the beforementioned Processes and by the following reactions from the other 4-ethynyl+-2-azetidinone derivative (I).

Process 8

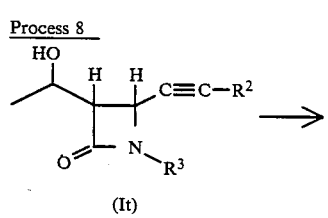

(It)

-continued

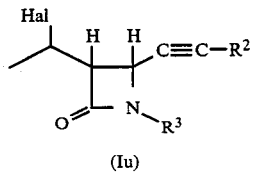
(Iu)

Process 9

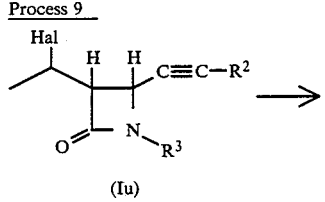
(Iu)

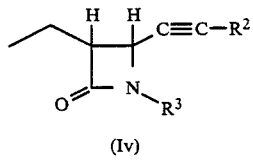
(Iv)

Process 10

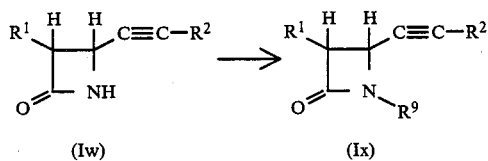
(Iw)　　　　(Ix)

Process 11

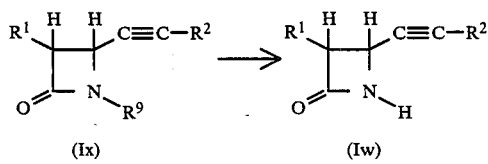
(Ix)　　　　(Iw)

Process 12

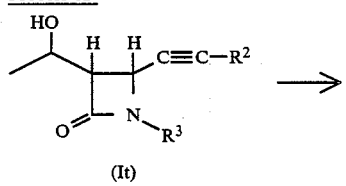
(It)

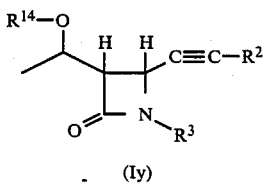
(Iy)

Process 13

(Iy)

-continued

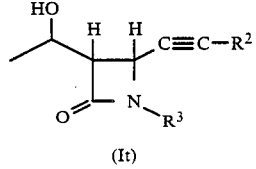
(It)

Process 14

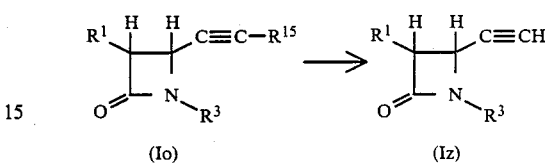
(Io)　　　　(Iz)

wherein, $R^1$, $R^2$ and $R^3$ are each as defined above,
Hal is a haloren,
$R^9$ and $R^{14}$, which may be the same or different, are protective groups, and
$R^{15}$ is a tri(lower alkyl)silyl group.

Suitable examples of "protective group" for $R^9$ are the same as exemplified before for $R^3$.

Suitable examples of "protective group" for $R^{14}$ are the same as exemplified before for the protected hydroxy for $R^1$.

PROCESS 8

The compound (Iu) can be prepared by reacting a compound (It) with halogenating agent in a conventional manner. The halogenating agent may include a hydrogen halide such as hydrogen bromide, hydrogen chloride, a phosphorus halide such as phosphorus tribromide, phosphorus pentachloride, triphenylphosphine-carbontetrachloride, triphenylphosphine-carbontetrabromide, thionyl chloride, etc.

The halogenation can be conducted in the presence or absence of sulfuric acid, zink chloride or pyridine in a solvent as exemplifed in Process 7.

PROCESS 9

The compound (Iv) can be prepared by reducing a compound (Iu). The reduction can be typically conducted by using a reducing agent such as metal (e.g. zinc, etc.) in the presence of an acid (e.g. acetic acid, hydrogen chloride, etc.), lithium aluminium hydride or lithium hydride in a conventional solvent as exemplified in Process 7.

PROCESS 10

The compound (Ix) can be prepared by reacting a compound (Iw) with a compound of the formula (VIII)

$$R^9-Y \qquad (VIII)$$

wherein, $R^9$ is as defined above, and Y is an acid residue.

Suitable examples of "acid residue" are halogen, mesyloxy, p-toluenesulfonyloxy and the like.

Suitable examples of the compound (VIII) are trimethylsilyl chloride, trimethylsilyl bromide, t-butyldimethylsilyl chloride, p-nitrobenzyl chloride, acetyl chloride, and the like.

The reaction can optionally be conducted in the presence of a base as exemplified before in Process 4.

Suitable examples of the solvent are the same as exemplified before in Process 7.

In case that the compound (Iw) having a free hydroxy group in its molecule, the compound (Iw) is treated with butyl lithium or lithium bis(trimethylsilyl)amide beforehand in an etheral solvent at a temperature below −60° C. followed by reacting a compound (VIII) to give a N-protected compound (Ix) having free hydroxy group.

PROCESS 11

The compound (Iw) can be prepared by subjecting a compound (Ix) to an elimination reaction of the protective group.

This reaction can be conducted by treating the compound (Ix) with a protonic acid such as concentrated hydrochloric acid in an aqueous solvent such as methanol, and then stirring the mixture at 0° C. to 100° C.

PROCESS 12

The compound (Iy) can be prepared by reacting a compound (It) with a compound (IX)

$$R^{14}-Y \quad (IX)$$

wherein, $R^{14}$ and Y are each as defined above.

Suitable examples of the compound (IX) and reaction conditions are the same as exemplified before in Process 10, provided that the reaction temperature can be selected from −10° C. to 100° C.

PROCESS 13

The compound (It) can be prepared by subjecting a compound (Iy) to a solvolysis. This reaction can be conducted in a similar manner to that of second step of the Process 4.

PROCESS 14

The compound (Iz) can be prepared by eliminating a tri(lower alkyl)silyl group of the compound (Io).

This reaction can be conducted by mild solvolysis, for example by reacting (Io) with cesium fluoride in the presence of a solvent such as water, an alcohol such as methanol, ethanol, etc., an ether, or the like at room temperature or under heating.

Further, the inventors of this invention could attain a conversion method of 3,4-cis-2-azetidinone derivative (X) to trans isomer (XI) by the following process.

Process 15 wherein, $R^3$, $R^4$, $R^5$, $R^7$, $R^{11}$, $R^{12}$, $R^{13}$ and X are each as defined above, Z is an organic residue.

Suitable examples of "organic residue" for Z are the same as the above-defined organic residue for $R^1$.

3,4-Trans-2-azetidinone derivative (XI) can be prepared by reacting a cis-compound (X) with a compound (VI) and then by subjecting the resultant to a solvolysis.

This reaction can be conducted in a similar manner to that of the above-mentioned Process 4. Therefore, suitable reaction condition can be referred to Process 4.

The object compounds in the above Processes 1 to 15 can be isolated from the reaction mixture and purified by a conventional manner.

In the above formula (I), the specific preferred examples of those are exemplified below.

Cis-3-[(R)-1-hydroxyethyl]-4-ethynyl-2-azetidinone,
trans-3-[(R)-1-hydroxyethyl]-4-trimethylsilylethynyl-2-azetidinone,
cis-3-[(R)-1-(t-butyldimethylsilyloxy)ethyl]-4-trimethylsilylethynyl-2-azetidinone,
(3S,4S)- and (3R,4R)-3-ethyl-4-trimethylsilylethynyl-2-azetidinone,
(3S,4S)- and (3R,4R)-3-(1-bromoethyl)-4-ethynyl-2-azetidinone,
(3S,4S)-3-[(R)-1-hydroxyethyl]-4-ethynyl-2-azetidinone,
(3S,4S)- and (3R,4S)-3-[(R)-1-hydroxyethyl]-4-trimethylsilylethynyl-2-azetidinone,
(3S,4S)-3-[(R)-1-(t-butyldimethylsilyloxy)ethyl]-4-trimethylsilylethynyl-2-azetidinone,
(3S,4S)-3-[(R)-1-(trimethylsilyloxy)ethyl]-4-trimethylsilylethynyl-2-azetidinone,
(3S,4S)-3-[(R)-1-(t-butyldimethylsilyloxy)ethyl]-4-trimethylsilylethynyl-1-trimethylsilyl-2-azetidinone,
(3S,4R)-3-[(R)-1formyloxyethyl]-4-trimethylsilylethynyl-2-azetidinone,
(3S,4R)-3-[(R)-1-(t-butyldimethylsilyloxy)ethyl]-4-ethynyl-2-azetidinone,
(3S,4R)-3-[(R)-1-benzoyloxyethyl]-4-trimethylsilylethynyl-2-azetidinone, and
(3S,4S)-3-acetyl-1-(t-butyldimethylsilyl)-4-trimethylsilylethynyl-2-azetidinone.

The following Examples are given for the purpose of illustrating this invention in more detail.

In the following Examples, the formulas Me and $$-Si\begin{cases}\\\\\end{cases}$$

mean methyl group and t-butyldimethylsilyl group respectively.

EXAMPLE 1

Synthesis of compounds (1) and (2)

Lithium bis(trimethylsilyl)amide is synthesized by dropwise addition of 5 ml of a commercial n-butyllithium (1.60M)-hexane solution to a solution of 1,1,1,3,3,3-hexamethyldisilazane (1.30 g) in dry tetrahydrofuran (15 ml) at −5° C. to 0° C. The mixture is stirred at 0° C. for 10 minutes and added dropwise to a solution of trimethylsilylpropynal (1.0 g) in dry tetrahydrofuran (5 ml) at −70° C. to −65° C., followed by further stirring at −70° C. for an hour to give a solution containing the corresponding trimethylsilylimine compound.

A solution containing lithium diisopropylamine is produced by dropwise addition of commercial n-butyllithiumhexane (13 ml) to a solution of diisopropylamine (2.0 g) in dry tetrahydrofuran (15 ml) at −5° C. to 0° C. This solution is cooled to −70° C., and a solution of ethyl 3-hydroxybutanoate (1.20 g) in dry tetrahydrofuran (5 ml) is added dropwise, followed by stirring at the same temperature for 1.5 hours. To this solution is added dropwise the above trimethylsilylimine compound solution with carefully maintaining the reaction temperature so as not to exceed −65° C. The mixture is stirred at −70° C. for 1.5 hours and then at room temperature for an additional 1.5 hours, poured into a mixture of 10% hydrochloric acid (30 ml) and ethyl acetate (250 ml) and adjusted to pH 3.0 with 10% hydrochloric acid. The organic layer is separated, washed with water, dried over magnesium sulfate and concentrated under reduced pressure. The thus-obtained brown residue is subjected to silica gel column chromatography (eluent: 23% ethyl acetate-hexane). The eluate is concentrated under reduced pressure and the residue is washed with n-hexane to give cis i.e. (3R,4S)-3-[(R)-1-hydroxyethyl]-4-trimethylsilylethynyl-2-azetidinone (0.20 g) as white crystals.

M.p.: 95°-97° C. IR (Nujol): 3360, 3190, 1755 cm$^{-1}$. NMR (CDCl$_3$, ppm): 0.10 (9H, s), 1.18 (3H, d, J=7.1 Hz), 2.74 (1H, d, J=3.3 Hz), 3.21 (1H, ddd, J=7.7, 6.7, 1.5 Hz), 4.12 (1H, m), 4.22 (1H, d, J=6.7 Hz), 6.50 (1H, m).

$[\alpha]_D^{20}$; −11.8° (C=1.12, EtOH).

On the other hand, the n-hexane washings are dried under reduced pressure to give 0.1 g of trans-3-(1-hydroxyethyl)-4-trimethylsilylethynyl-2-azetidinone as an oil.

IR (Nujol): 3300, 1770(sh), 1740, 1720 cm$^{-1}$. NMR (CDCl$_3$, ppm): 0.10 (9H, s), 1.10 (3H, m), 2.10 (1H, m), 3.18 (1H, dd, J=3.3 and 3.3 Hz), 4.06 (1H, d, J=3.3 Hz), 4.16 (1H, m), 6.23 (1H, m).

EXAMPLE 2

Synthesis of compounds (1) and (2)

In an argon stream, 1,1,1,3,3,3-hexamethyldisilazane (3.8 g) is dissolved in dry tetrahydrofuran (20 ml), and a commercial n-butyllithium (1.6M)-hexane solution (15 ml) is added dropwise to the solution at −10° C. to −5° C. to produce a solution containing lithium bis(trimethylsilyl)amide. This solution is stirred at −10° C. for 0.5 hour, and a solution of trimethylsilylpropynal (3.0 g) in dry tetrahydrofuran (4 ml) is added dropwise with maintaining the reaction temperature so as not to exceed −68° C. After completion of the addition, the mixture is stirred at −75° C. for an hour to give a solution containing the corresponding trimethylsilylimine compound.

In an argon stream, 1,1,1,3,3,3-hexamethyldisilazane (8 g) is reacted with a n-butyllithium-hexane solution (30 ml) in the same manner as above to give a solution containing lithium bis(trimethylsilyl)amide. A solution of ethyl 3-hydroxybutanoate (2.6 g) in dry tetrahydrofuran (4 ml) is gradually added dropwise thereto at −68° C. or lower, followed by stirring at −70° C. or lower for an hour. To the mixture is added the above trimethylsilylimine compound-containing solution at −70° C. or lower, and the resulting mixture is stirred at the same temperature for an hour and then at 3° C. for an additional one hour. The mixture is poured into a mixture of ethyl acetate (200 ml), aqueous sodium chloride (200 ml) and acetic acid (20 ml) and adjusted to pH 3.8 with 6N hydrochloric acid. The organic layer is separated, washed with aqueous sodium chloride and adjusted to pH 7.5 with aqueous sodium hydrogen carbonate. The organic layer is separated, washed with aqueous sodium chloride, dried over magnesium sulfate and concentrated under reduced pressure. To the residue is added n-hexane (50 ml) and the mixture is allowed to stand at room temperature for 15 hours. The resulting crystals are collected by filtration to give 1.35 g of cis-3-[(R)-1-hydroxyethyl]-4-trimethylsilylethynyl-2-azetidinone. The physical characteristics of this product are identical with those of the compound obtained in Example 1.

The n-hexane mother liquor is purified by silica gel column chromatography to give 3-(1-hydroxyethyl)-4-trimethylsilylethynyl-2-azetidinone (1.54 g) with the cis-trans ratio of 1:2.

IR (Nujol): 3350, 3200, 2150, 1760, 1740 cm$^{-1}$. NMR (CDCl$_3$, ppm): 0 (9H, s), 1.13 and 1.20 (3H, d, J=6.6 Hz), 2.90 (1H, m), 3.17 (1H, m), 4.13 (2H, m), 6.7 and 6.80 (1H, m).

EXAMPLE 3

Synthesis of compounds (1) and (2)

In an argon stream, dry tetrahydrofuran (10 ml), 1,1,1,3,3,3-hexamethyldisilazane (1.1 ml), a commercial n-butyllithium (1.16M)-hexane solution (3 ml), trimethylsilylpropynal (0.6 g) and dry tetrahydrofuran (2 ml) are worked up in the same manner as Example 1 to give a solution containing the corresponding trimethylsilylimine compound.

In an argon stream, dry tetrahydrofuran (10 ml), diisopropylamine (1.7 ml) and a n-butyllithium-hexane solution (7 ml) are treated in the same manner as Example 1 to give a lithium-diisopropylamine solution. To this solution is added dropwise a solution of ethyl 3-hydroxybutanoate (0.65 g) in dry tetrahydrofuran (2 ml) with care that the reaction temperature does not exceed −68° C. and, after completion of the addition, the mixture is stirred at −70° C. for 40 minutes. After addition of triisopropylboron (2.3 ml) at the same temperature, the mixture is stirred for an hour. To this solution is added the above trimethylsilylimine compound-containing solution at −68° C. or lower, and the mixture is stirred at the same temperature for 30 minutes and then at 3° C. for an hour. To the reaction mixture is added acetic acid (3 ml) and the resulting mixture is poured into a mixture of ethyl acetate (70 ml) and aqueous sodium chloride (50 ml). The organic layer is separated, washed with aqueous sodium chloride, aqueous sodium hydrogen carbonate and aqueous sodium chloride in that order, dried over magnesium sulfate and concentrated under reduced pressure. The residue is subjected to silica gel column chromatography to give 0.29 g of 3-(1-hydroxyethyl)-4-trimethylsilylethynyl-2-azetidinone (cis-trans ratio: 1:2).

EXAMPLE 4

Synthesis of compound (3)

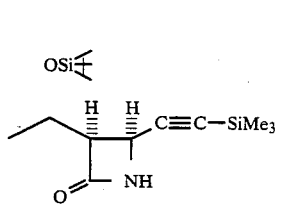

Imidazole (0.2 g) and tert-butyldimethylsilyl chloride (0.3 g) are added to a solution of cis-3-[(R)-1-hydroxyethyl]-4-trimethylsilylethynyl-2-azetidinone (0.2 g) in N,N-dimethylformamide (7 ml), and the mixture is stirred at 60° C.–65° C. for 1.5 hours and then poured into a mixture of ethyl acetate (50 ml) and water (50 ml). The organic layer is separated, washed with aqueous sodium chloride, dried over magnesium sulfate and concentrated under reduced pressure, and the residue is subjected to silica gel column chromatography to give cis i.e. (3R,4S)-3-[(R)-1-(tert-butyldimethylsilyloxy)ethyl]-4-trimethylsilylethynyl-2-azetidinone as crystals. (0.24 g).

$[\alpha]_D^{14}$: −20.6° (C=1.01, EtOH). IR (Nujol): 3200, 2150, 1765 cm$^{-1}$ NMR (CDCl$_3$, ppm): 0 (15H, s), 0.9 (9H, s), 1.30 (3H, d, J=6.6 Hz), 3.30 (1H, m), 4.30 (1H, d, J=6.0 Hz), 4.30 (1H, m), 6.17 (1H, m).

EXAMPLE 5

Synthesis of compound (15)

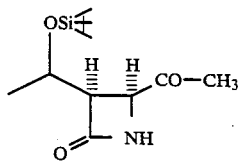

Cis-3-[(R)-1-(tert-butyldimethylsilyloxy)ethyl]-4-trimethylsilylethynyl-2-azetidinone (0.24 g) is dissolved in a mixture of tetrahydrofuran (5 ml) and water (1 ml), and mercury sulfate (0.03 g) and concentrated sulfuric acid (0.06 g) are added, followed by stirring at room temperature for 15 hours. After addition of sodium hydrogen carbonate (0.2 g), the reaction mixture is poured into ethyl acetate-water, and the organic layer is separated, washed with aqueous sodium chloride, dried over magnesium sulfate and concentrated under reduced pressure. The residue is subjected to silica gel column chromatography to give 0.03 g of cis-4-acetyl-3-[1-(tert-butyldimethylsilyloxy)ethyl]-2-azetidinone.

IR (Nujol): 2950, 1760, 1720 cm$^{-1}$. NMR (CDCl$_3$, ppm): 0 (6H, s), 0.9 (9H, s), 1.33 (3H, d, J=6.2 Hz), 2.30 (3H, s), 3.73 (1H, dd, J=6.2 and 3.3 Hz), 4.20 (1H, d, J=6.0 Hz), 4.40 (1H, dd, J=6.0 and 3.3 Hz), 6.67 (1H, m).

EXAMPLE 6

Synthesis of compounds (3) and (4)

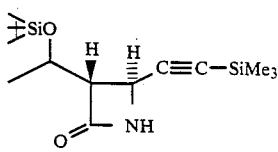

A cis/trans mixture (1.44 g) of 3-(1-hydroxyethyl)-4-trimethylsilylethynyl)-2-azetidinone is dissolved in N,N-dimethylformamide (15 ml), and imidazole (1.4 g) and tert-butyldimethylsilyl chloride (3.0 g) are added. The mixture is stirred at 60° C. for 2 hours and then poured into a mixture of ethyl acetate (100 ml) and water (50 ml). The organic layer is separated, serially washed with water and aqueous sodium chloride, dried over magnesium sulfate and concentrated under reduced pressure. The residue is subjected to silica gel column chromatography to give 0.62 g of cis-3-[(R)-1-(tert-butyldimethylsilyloxy)ethyl]-4-trimethylsilylethynyl-2-azetidinone, 0.97 g of trans-3-[1-(tert-butyldimethylsilyloxy)ethyl]-4-trimethylsilylethynyl-2-azetidinone and 0.36 g of a cis/trans mixture. The physical characteristics of the cis form are identical with those of the compound obtained in Example 4. Physical characteristics of the trans compound IR (Nujol): 3150, 3100, 2200, 1760, 1720 cm$^{-1}$. NMR (CDCl$_3$, ppm): 0 (15H, m), 0.83 (9H, m), 1.20 and 1.27 (3H, d, J=6.7 Hz), 3.23 and 3.37 (1H, m), 4.13 and 4.30 (1H, d, J=3 Hz), 4.23 (1H, m), 6.47 (1H, m).

EXAMPLE 7

Synthesis of compound (16)

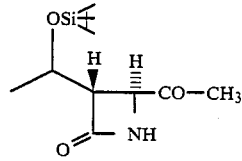

trans-3-[1-(tert-Butyldimethylsilyloxy)ethyl]-4-trimethylsilylethynyl-2-azetidinone (1.2 g) is dissolved in a mixture of tetrahydrofuran (20 ml) and water (2 ml), and mercury sulfate (0.07 g) and concentrated sulfuric acid (catalytic amount) are added, followed by stirring at room temperature for 15 hours. The reaction mixture is poured into a mixture of ethyl acetate (150 ml) and water (100 ml) and the organic layer is separated, washed with aqueous sodium chloride, dried over magnesium sulfate and concentrated under reduced pressure to give 0.60 g of trans-4-acetyl-3-[1-(tert-butyldimethylsilyloxy)ethyl]-2-azetidinone.

IR (Nujol): 3200, 1745 (sh), 1740, 1705 cm$^{-1}$. NMR (CDCl$_3$, ppm): 0 (6H, s), 0.83 (9H, s), 1.23 and 1.28 (3H, d, J=6.7 Hz), 2.17 and 2.20 (3H, s), 3.03 and 3.17 (1H, m), 4.10 and 4.20 (1H, d, J=3 Hz), 4.23 (1H, m), 6.63 (1H, m).

EXAMPLE 8

Synthesis of compound (17)

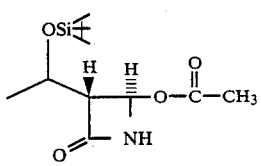
(17)

m-Chloroperbenzoic acid (1 g) is added to a solution of trans-4-acetyl-3-[1-(tert-butyldimethylsilyloxy)ethyl]-2-azetidinone (0.23 g) in chloroform (15 ml), and the mixture is allowed to stand at room temperature for 15 hours and then poured into a mixture of ethyl acetate (100 ml), 5% aqueous sodium thiosulfate (50 ml) and aqueous sodium hydrogen carbonate (30 ml). The organic layer is separated, washed with aqueous sodium chloride, dried over magnesium sulfate and concentrated under reduced pressure to give 0.23 g of trans-4-acetoxy-3-[1-(tert-butyldimethylsilyloxy)ethyl]-2-azetidinone.

IR (Nujol): 3250, 1780, 1750 cm$^{-1}$. NMR (CDCl$_3$, ppm): 0 (6H, s), 0.87 (9H, s), 1.23 and 1.32 (3H, d, J=7.3 Hz), 2.10 (3H, s), 3.23 (1H, m), 4.30 (1H, m), 5.73 and 5.90 (1H, broad s), 6.87 (1H, m).

EXAMPLE 9

Synthesis of compound (18)

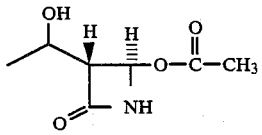
(18)

Trans-4-acetoxy-3-[1-(tert-butyldimethylsilyloxy)-ethyl]-2-azetidinone (0.20 g) is dissolved in a mixture of acetic acid (5 ml) and water (2 ml), and the solution is stirred at 70°–80° C. for 2.5 hours and then concentrated under reduced pressure. The residue is subjected to silica gel column chromatography to give 0.03 g of trans-4-acetoxy-3-(1-hydroxyethyl)-2-azetidinone.

IR (Neat): 3300, 1750, 1680 cm$^{-1}$. NMR (CDCl$_3$, ppm): 1.37 and 1.43 (3.3H, d, J=6.6 Hz), 2.13 (3H, s), 2.83 and 3.13 (1H, m), 3.23 (1H, m), 4.20 (1H, m), 5.77 and 5.87 (1H, broad s), 7.13 (1H, m).

EXAMPLE 10

Synthesis of compounds (5) and (6)

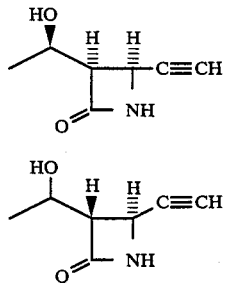
(5)

(6)

A cis/trans mixture (1.0 g) of 3-(1-hydroxyethyl)-4-trimethylsilylethynyl-2-azetidinone is dissolved in a mixture of tetrahydrofuran (10 ml) and methanol (5 ml), and a solution of cesium fluoride (0.2 g) in water (2 ml) is added to the solution. The mixture is stirred at 60° C. for an hour and concentrated under reduced pressure and the residue is extracted with ethyl acetate (20 ml) and tetrahydrofuran (20 ml). The extract is dried over magnesium sulfate, concentrated under reduced pressure and crystallized from ethyl acetate to give 0.18 g of cis-3-[(R)-1-hydroxyethyl]-4-ethynyl-2-azetidinone.

The ethyl acetate mother liquor is subjected to silica gel column chromatography to give 0.10 g of trans-3-(1-hydroxyethyl)-4-ethynyl-2-azetidinone and a cis/trans mixture (0.3 g). Physical characteristics of the cis compound IR (Nujol): 3400, 3250, 3200, 2100, 1740 cm$^{-1}$. NMR (CDCl$_3$, ppm): 1.37 (3H, d, J=6.6 Hz), 2.57 (1H, d, J=2.5 Hz), 2.77 (1H, d, J=3.0 Hz), 3.37 (1H, m), 4.30 (1H, m), 4.43 (1H, dd, J=6.6, 2.5 Hz), 6.50 (1H, m). Physical characteristics of the trans compound IR (Chloroform): 3400, 3300, 2250, 1760 cm$^{-1}$. NMR (CDCl$_3$, ppm): 1.33 and 1.40 (3H, d, J=6.6 Hz), 2.57 (1H, d, J=2.0 Hz), 2.87 and 3.87 (1H, m), 3.43 (1H, m), 4.20 (1H, m), 4.30 and 4.47 (1H, dd, J=3.3 and 2.0 Hz), 7.20 (1H, m).

EXAMPLE 11

Synthesis of compound (19)

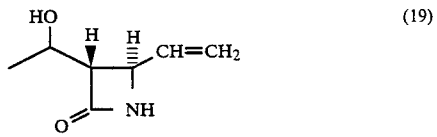
(19)

A solution of trans-3-(1-hydroxyethyl)-4-ethynyl-2-azetidinone (0.10 g) in ethanol (5 ml) is subjected to catalytic reduction with hydrogen gas in the presence of Lindlar catalyst (0.01 g). The reduction is continued until 14 ml of hydrogen gas has been absorbed. The catalyst is then filtered off and the filtrate is concentrated under reduced pressure to give 0.1 g of trans-3-(1-hydroxyethyl)-4-vinyl-2-azetidinone.

IR (Chloroform): 3400, 1750, 1660 cm$^{-1}$. NMR (CDCl$_3$, ppm): 1.33 (3H, m), 2.96 (1H, m), 3.40 (1H, m), 4.17 (2H, m), 5.27 (1H, d, J=10.6 Hz), 5.40 (1H, d, J=18.0 Hz), 6.00 (1H, m), 6.73 (1H, m).

EXAMPLE 12

Synthesis of compound (20)

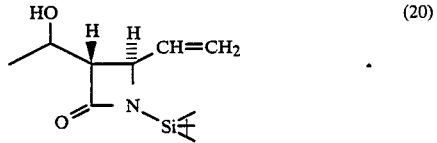
(20)

In an argon stream, a solution of trans-3-(1-hydroxyethyl)-4-vinyl-2-azetidinone (0.10 g) in dry tetrahydrofuran (10 ml) is cooled to −75° C. and a commercial n-butyllithium (1.6M)-hexane solution (0.9 ml) is added dropwise to the solution while maintaining a temperature at −65° C. or lower. The mixture is stirred at −75° C. for an hour and a solution of tert-butyldimethylsilyl chloride (0.16 g) in dry tetrahydrofuran (2 ml) is added dropwise at −70° C. or lower. The reaction mixture is further stirred at −73° C. for 0.5 hour and poured into a mixture of ethyl acetate (70 ml), water (50 ml) and acetic acid (2 ml). The organic layer is separated, adjusted to pH 7.0 with aqueous sodium hydrogen carbonate, washed with aqueous sodium chloride, dried over magnesium sulfate and concentrated under reduced pressure to give 0.1 g of trans-3-(1-hydroxyethyl)-1-(tert-butyldimethylsilyl)-4-vinyl-2-azetidinone.

IR (Neat): 3400, 1740 (sh), 1720, 1660 cm$^{-1}$. NMR (CDCl$_3$, ppm): 0 (6H, s), 0.80 (6H, s), 0.80 (9H, s), 1.17 (3H, m), 2.90 (1H, m), 3.20 (1H, m), 4.10 (2H, m), 5.17 (1H, d, J=10.0 Hz), 5.30 (1H, d, J=17.0 Hz), 5.90 (1H, m).

EXAMPLE 13

Synthesis of compound (7)

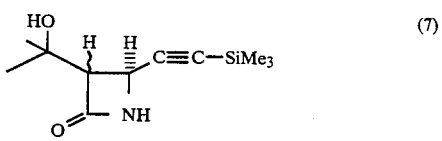

The reaction procedure of Example 1 is followed using trimethylsilylpropynal (1.26 g), 1,1,1,3,3,3-hexamethyldisilazane (0.61 g) and commercial butyllithium (1.60M)-hexane (6.2 ml) as well as ethyl 3-hydroxy-3-methylbutanoate (1.46 g), diisopropylamine (2.40 g) and commercial butyllithium-hexane (14 ml). The reaction mixture containing the desired product is concentrated under reduced pressure and the residue is subjected to silica gel column chromatography (eluent: 30% ethyl acetate-70% hexane) to give 0.278 g of 3-(1-hydroxy-1-methylethyl)-4-trimethylsilylethynyl-2-azetidinone (1:2 cis-trans mixture).

M.p.: 137°-140° C. IR (Nujol): 3500, 3260, 2960, 1735, 1710 cm$^{-1}$. NMR (CDCl$_3$, ppm) of the cis compound 0.10 (9H, s), 1.33 (6H, s), 2.86 (1H, s) 3.33 (1H, dd, J=6.3 and 2.0 Hz), 4.30 (1H, d, J=6.3 Hz), 6.47 (1H, m). NMR (CDCl$_3$, ppm) of the trans compound 0.10 (9H, s), 1.13 (3H, s), 1.40 (3H, s), 2.06 (1H, s), 3.16 (1H, d, J=3.3 Hz), 4.13 (1H, d, J=3.3 Hz), 6.30 (1H, m).

EXAMPLE 14

Synthesis of compounds (8) and (9)

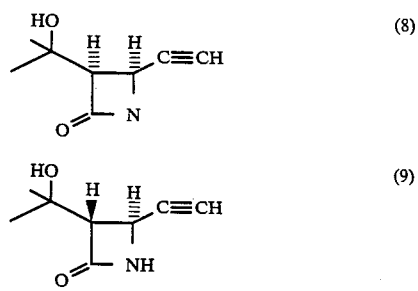

A solution of cesium fluoride (0.05 g) in water (3 ml) is added to a mixture of 3-(1-hydroxy-1-methylethyl)-4-trimethylsilylethynyl-2-azetidinone (0.143 g) (cis-trans mixture), tetrahydrofuran (10 ml) and methanol (3 ml). The mixture is refluxed for 0.5 hour and then poured into a mixture of ethyl acetate (100 ml and water (50 ml). The organic layer is separated, washed with aqueous sodium chloride and dried over magnesium sulfate, followed by removal of the solvent by distillation under reduced pressure. The residue is subjected to silica gel column chromatography (eluent: 30–40% ethyl aceta-te/60–70% hexane). The first fraction gives 0.04 g of trans-3-(1-hydroxy-1-methylethyl)-4-ethynyl-2-azetidinone.

IR (Neat): 3400, 3200, 1750 (sh), 1740 cm$^{-1}$. NMR (CDCl$_3$, ppm): 1.28 (3H, s), 1.43 (3H, s), 2.59 (1H, d, J=2.4 Hz), 2.83 (1H, m), 3.30 (1H, d, 3.0 Hz), 4.27 (1H, dd, J=3.0 and 2.4 Hz), 6.83 (1H, m).

The second fraction gives 0.022 g of cis-3-(1-hydroxy-1-methylethyl)-4-ethynyl-2-azetidinone.

M.p.: 82°-85° C. IR (Nujol): 3250, 3480, 3300, 3200, 1750 (sh), 1740 cm$^{-1}$. NMR (CDCl$_3$, ppm): 1.46 (6H, s), 2.67 (2H, m), 3.56 (1H, dd, J=6.0 and 1.5 Hz), 4.43 (1H, dd, 6.0 and 2.4 Hz), 6.50 (1H, m).

EXAMPLE 15

Synthesis of compounds (10) and (11)

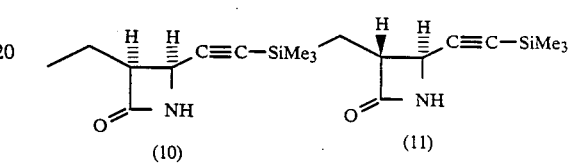

The reaction procedure of Example 1 is followed in an argon stream using 1,1,1,3,3,3-hexamethyldisilazane (0.78 g), commercial n-butyllithium (1.6M)-hexane (3 ml), dry tetrahydrofuran (10 ml) and trimethylsilylpropynal (0.6 g) as well as diisopropylamine (0.9 ml), dry tetrahydrofuran (10 ml), commercial n-butyllithium (1.6M)-hexane (3.2 ml) and ethyl butanoate (0.6 g) to give a tetrahydrofuran solution containing the desired compound. After addition of acetic acid (2 ml), the mixture is poured into a mixture of ethyl acetate (70 ml) and water (50 ml). The organic layer is separated, washed with aqueous sodium hydrogen carbonate and aqueous sodium chloride in that order, dried over magnesium sulfate and evaporated under reduced pressure. The residue is subjected to silica gel column chromatography (eluent: 1:9 ethyl acetate-hexane mixture). The first, second and third fractions give trans-3-ethyl-4-trimethylsilylethynyl-2-azetidinone (0.05 g), cis-trans mixture (0.13 g) and cis compound (0.19 g), respectively.

Physical characteristics of the cis compound

IR (Neat): 3250, 2150, 1750 cm$^{-1}$. NMR (CDCl$_3$, ppm): 0 (9H, s), 0.97 (3H, t, J=7.3 Hz), 1.73 (2H, m), 3.10 (1H, m), 4.22 (1H, d, J=6.7 Hz), 6.20 (1H, m).

Physical characteristics of the trans compound

IR (Neat): 3250, 2150, 1760 cm$^{-1}$. NMR (CDCl$_3$, ppm): 0 (9H, s), 1.00 (3H, t, J=7.3 Hz), 1.70 (2H, m), 3.13 (1H, m), 3.83 (1H, d, J=3.0 Hz), 6.30 (1H, s).

EXAMPLE 16

Synthesis of compound (12)

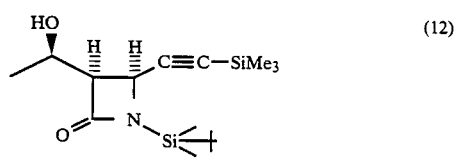

Cis-3-[(R)-1-hydroxyethyl]-4-trimethylsilylethynyl-2-azetidinone (0.8 g) is dissolved in dry tetrahydrofuran (15 ml) in an argon stream, and the solution is cooled to —70° C. followed by dropwise addition of n-butyllithium (1.6M)-hexane (4.8 ml) while carefully maintaining the temperature so as not to exceed —65° C. To the mixture is added dropwise a solution of tert-butyldimethylsilyl chloride (0.86 g) in dry tetrahydrofuran (5 ml) at —70° C. or lower, and the resulting mixture is stirred at the same temperature for an hour and then poured into a mixture of ethyl acetate (100 ml) and water (100 ml). The organic layer is separated, washed with aqueous sodium chloride and dried over magnesium sulfate. The solvent is then distilled off under reduced pressure and the residue is subjected to silica gel column chromatography (eluent: 1:9 ethyl acetate-n-hexane mixture) to give 0.40 g of cis-1-(tert-butyldimethylsilyl)-3-[(R)-1-hydroxyethyl]-4-trimethylsilylethynyl-2-azetidinone.

IR (Nujol): 3350, 2300, 1720, cm$^{-1}$. NMR (CDCl$_3$, ppm): 0 (9H, s), 0.10 (6H, s), 0.83 (9H, s), 1.20 (3H, d, J=6.6 Hz), 2.83 (1H, m), 3.23 (1H, dd, J=6.6 and 6.6 Hz), 4.13 (1H, m), 4.20 (1H, d, J=6.6 Hz).

Cis-3-(1-hydroxyethyl)-4-trimethylsilylethynyl-2-azetidinone (0.20 g) is recovered from another eluate fraction.

EXAMPLE 17

Synthesis of compound (13)

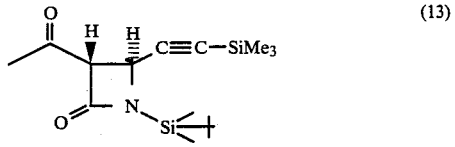
(13)

In an argon stream, a solution of dry trifluoroacetic acid (0.2 ml) in methylene chloride (3 ml) is added dropwise to a mixture of dimethyl sulfoxide (0.1 ml) and methylene chloride (10 ml) at —65° C. or lower, and the mixture is stirred at —70° C. for 0.5 hours. A solution of cis-1-(tert-butyldimethylsilyl)-3-[(R)-1-hydroxyethyl]-4-trimethylsilylethynyl-2-azetidinone (0.4 g) in methylene chloride (4 ml) is added dropwise at —65° C. or lower and the mixture is stirred at the same temperature for 0.5 hour. After addition of triethylamine (0.3 ml) at the same temperature, the temperature is gradually raised to room temperature. The reaction mixture is poured into a mixture of ethyl acetate (70 ml) and water (100 ml), and the organic layer is separated, washed with aqueous sodium chloride, dried over magnesium sulfate and concentrated under reduced pressure. The residue is subjected to silica gel column chromatography (eluent: 3% ethyl acetate-97% n-hexane) to give trans i.e. (3S,4S)-3-acetyl-1-(tert-butyldimethylsilyl)-4-trimethylsilylethynyl-2-azetidinone (0.13 g)

IR (Neat): 2150, 1750, 1705 cm$^{-1}$. NMR (CDCl$_3$, ppm): 0 (9H, s), 0.10 (6H, s), 0.90 (9H, s), 2.20 (3H, s), 4.23 (1H, d, J=3.0 Hz), 4.53 (1H, d, J=3.0 Hz).

EXAMPLE 18

Synthesis of compound (13)

Cis-1-(tert-butyldimethylsilyl)-3-[(R)-1-hydroxyethyl]-4-trimethylsilylethynyl-2-azetidinone (0.15 g) is dissolved in ethyl acetate (20 ml), and 5 g of activated manganese dioxide is added, followed by stirring at 25° C. for 5 hours. The manganese dioxide is filtered off and the filtrate is concentrated to give trans-3-acetyl-1-(tert-butyldimethylsilyl)-4-trimethylsilylethynyl-2-azetidinone (0.14 g).

EXAMPLE 19

Synthesis of compounds (14') and (14)

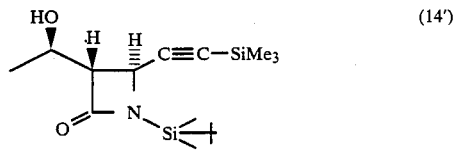
(14')

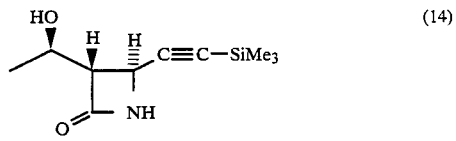
(14)

In an argon stream, trans i.e. (3S,4S)-3-acetyl-1-(tert-butyldimethylsily)-4-trimethylsilylethynyl-2-azetidinone (0.2 g) is dissolved in diethyl ether (15 ml), and 1.5 ml of a THF solution of K-selectride ®, which is commercially available, is added dropwise at 25° C. After completion of the addition, the mixture is stirred at the same temperature for 30 minutes and poured into a mixture of 50 ml of ethyl acetate and 50 ml of water. The organic layer is washed with brine, dried over magnesium sulfate and concentrated under reduced pressure. The residue is dissolved in methanol (15 ml), followed by addition of 0.3 ml of concentrated hydrochloric acid and stirring at 25° C. for an hour. The mixture is poured into a mixture of 70 ml of ethyl acetate and 50 ml of water, followed by phase separation, washing with brine, drying over magnesium sulfate and concentration under reduced pressure. The residue is subjected to silica gel column chromatography (eluent: 30% ethyl acetate-20% n-hexane) to give trans i.e. (3S,4S)-3-[(R)-1-hydroxyethyl]-4-trimethylsilylethynyl-2-azetidinone(14) (0.08 g).

IR (Nujol): 3370, 3200, 2200, 2740 cm$^{-1}$. NMR (CDCl$_3$, ppm): 1.20 (3H, d, J=6.5 Hz), 3.20 (2H, m), 4.10 (1H, m), 4.23 (1H, d, J=2.5 Hz), 6.67 (1H, m), 0.10 (9H, s).

[α]$_D^{25}$: +47.2° (C=0.72, CHCl$_3$).

EXAMPLE 20

Synthesis of compounds (21) and (22)

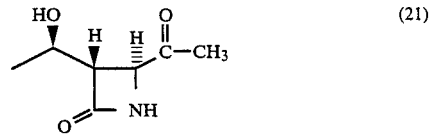
(21)

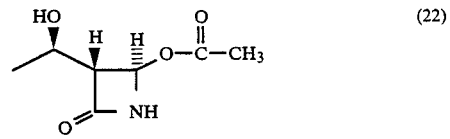
(22)

trans i.e. (3S,4S)-3-[(R)-1-hydroxyethyl]-4-trimethylsilylethynyl-2-azetidinone (0.08 g) is dissolved in a mixture of tetrahydrofuran (10 ml) and water (2 ml), and 0.02 g of mercury sulfate and a catalytic amount of concentrated sulfuric acid are added, followed by stirring at 25° C. for 3 hours. After addition of 0.1 g of sodium hydrogen carbonate, the mixture is concentrated to dryness under reduced pressure. The residue is extracted with 50 ml of ethyl acetate and the extract is concentrated to dryness. The residue is dissolved in 10 ml of ethyl acetate, and m-chloroperbenzoic acid (0.2 g) is added, followed by stirring for 50 hours. After addition of 0.2 ml of dimethyl sulfide, and the mixture is stirred further for 30 minutes and concentrated under reduced pressure. The residue is subjected to silica gel column chromatography (eluent: 60% ethyl acetate-40% n-hexane) to give trans i.e. (3S,4R)-4-acetoxy-3-[(R)-1-hydroxyethyl]-2-azetidinone (0.04 g).

IR (Nujol): 3300, 1750, 1680 cm$^{-1}$. NMR (CDCl$_3$, ppm): 1.23 (3H, d, J=6.6 Hz), 2.06 (3H, s), 3.16 (1H, m), 4.13 (1H, m), 5.80 (1H, m), 7.00 (1H, m).

EXAMPLE 21

Methyl R-(−)-3-hydroxybutanoic acid is reacted instead of ethyl 3-hydroxybutanoic acid according to a similar manner to that of Example 1 to give a compound (1).

The object compound is ascertained the compound (1) from the physical data.

EXAMPLE 22

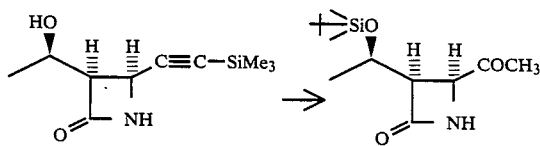

The object compound (0.15 g) of Example 1 is silylated by using tert-butyldimethylsilyl chloride (0.21 g), imidazole (0.15 g) and DMF (10 ml) according to Example 2 to give (3R,4S)-3-[(R)-1-(tert-butyldimethylsilyloxy)ethyl]-4-trimethylsilylethynyl-2-azetidinone. Without isolation, the above obtained compound is dissolved in a mixture of methanol (13 ml) and water (2 ml), and mercuric sulfate (0.1 g), ammonium sulfate (0.3 g) and concentrated sulfuric acid (trace) are added, followed by stirring at room temperature for 2 hours. The reaction mixture is poured into a mixture of ethyl acetate (100 ml) and water (50 ml), and the organic layer is separated, washed with brine, dried over magnesium sulfate and concentrated under reduced pressure. The residue is subjected to silica gel column chromatography (eluent: 30% ethyl acetate-70% hexane) to give 0.1 g of (3R,4S)-4-acetyl-3-[(R)-1-(tert-butyldimethylsilyloxy)ethyl]2-azetidinone.

IR (Nujol): 2950, 1760, 1720 cm$^{-1}$. NMR (CDCl$_3$, ppm): 0.1 (6H, s), 0.9 (9H, s), 1.37 (3H, d, J=6.9 Hz), 2.43 (3H, s), 3.77 (1H, m), 4.27 (1H, d, J=6.0 Hz), 4.47 (1H, m), 6.90 (1H, m).

EXAMPLE 23

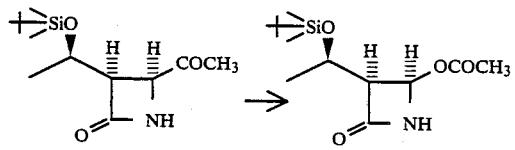

m-Chloroperbenzoic acid (0.5 g) is added to a solution of the object compound of Example 22 (0.08g) in ethyl acetate (8 ml), and the mixture is stirred at room temperature for 3 days and then poured into a mixture of ethyl acetate (50 ml), aqueous sodium hydrogen carbonate (20 ml) and dimethyl sulfide (0.4 ml). The mixture is stirred at room temperature for 30 minutes. The organic layer is separated, washed with brine, dried over magnesium sulfate and concentrated under reduced pressure. The residue is subjected to silica gel column chromatography (eluent: 15% ethyl acetate-85% hexane) to give 0.045 g of (3S,4R)-4-acetoxy-3-[(R)-1-(tert-butyldimethylsilyloxy)ethyl]-2-azetidinone.

$[\alpha]_D^{20}$ +22.4° (C=0.90, EtOH). IR (Nujol): 3250, 1780, 1720 cm$^{-1}$.

NMR (CDCl$_3$, ppm): 0.1 (6H, s), 1.0 (9H, s), 1.33 (3H, d, J==6.6 Hz), 2.16 (3H, s), 3.43 (1H, m), 4.33 (1H, m), 5.97 (1H, d, J=4.5 Hz), 6.67 (1H, m).

This compound was ascertained an anomer of (3R,4S)-4-acetoxy-3-[(R)-1-(tert-butyldimethylsilyloxy)-ethyl]-2-azetidinone which was known in the Tetrahedron Letters, Vol. 22, No. 51, pp 5205–5208 by comparison with the angle of rotation and the other physical data.

EXAMPLE 24

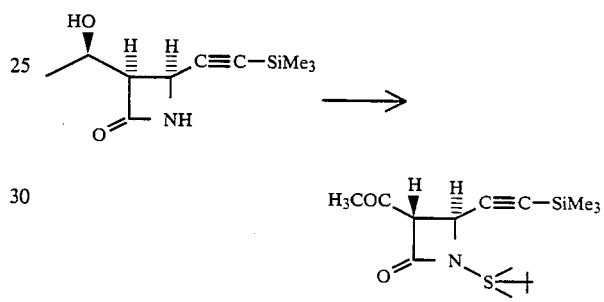

In an argon stream, a solution of LHDS is prepared by reacting 1,1,1,3,3,3-hexamethyldisilazane (0.45 ml) and n-butyllithium (1.3 ml) in dry tetrahydrofuran (10 ml) according to a similar manner to that of first half of Example 1. The above obtained solution containing LHDS is cooled to −70° C., followed by dropwise addition of a solution of tetrahydrofuran (5 ml) containing the object compound (0.21 g) of Example 1 while maintaining the temperature so as not to exceed −65° C. After stirring at the same temperature for an hour, a solution of tert-butyldimethylsilyl chloride (0.15 g) in dry tetrahydrofuran (3 ml) is added thereto at −65° C. or lower, followed by stirring at −60° C. for another an hour and then at room temperature for 1.5 hour. The mixture is poured into a mixture of ethyl acetate (100 ml) and water (50 ml). The organic layer is separated, washed with brine and dried over magnesium sulfate. The solvent is then distilled off under reduced pressure to give a residue containing a crude N-silylated compound. The residue containing N-silylated compound is dissolved in ethyl acetate (20 ml), and 20 g of activated manganese dioxide is added, followed by stirring at 25° C. for 15 hours. The manganese dioxide is filtered off and the filtrate is concentrated under reduced pressure. The residue is subjected to silica gel column chromatography (eluent: 2% ethyl acetate-98% hexane) to give 0.15 g of (3S,4S)-3-acetyl-1-(tert-butyldimethylsilyl)-4-trimethylsilylethynyl-2-azetidinone.

$[\alpha]_D^{24}$ +7.3° (C=1.70, CHCl$_3$).

The object compound was ascertained the same obtained by the Example 17 from the Physical data.

EXAMPLE 25

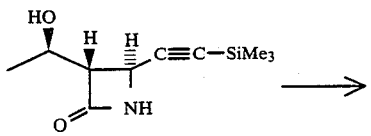

Imidazole (0.1 g) and tert-butyldimethylsilyl chloride (0.08 g) are added to a solution of the object compound (0.036 g) of Example 6 in DMF (5 ml) at 40° C. and the mixture is stirred at the same temperature for 2 hours and then poured into a mixture of ethyl acetate (50 ml) and water (30 ml). The organic layer is separated, washed with brine, dried over magnesium sulfate and concentrated under reduced pressure. The residue is dissolved in a mixture of tetrahydrofuran (7 ml) and water (2 ml), and stirred at 25° C. for 4 hours in the presence of a trace of concentrated sulfuric acid. The reaction mixture is poured into a mixture of ethyl acetate (50 ml) and water (30 ml) and the organic layer is separated, washed with brine, dried over magnesium sulfate and concentrated under reduced pressure. Thus obtained residue is dissolved in ethyl acetate (12 ml) and m-chloroperbenzoic acid (0.3 g) is added thereto. The mixture is stirred at room temperature for 2 days and then poured into a mixture of ethyl acetate (50 ml), saturated sodium bicarbonate solution (20 ml) and dimethyl sulfide (0.15 ml) followed by stirring. The organic layer is separated, washed with brine, dried over magnesium sulfate and concentrated under reduced pressure. The residue is subjected to silica gel column chromatography (eluent: 15% ethyl acetate-85% hexane) to give 0.012 g of (3R,4R)-4-acetoxy-3-[(R)-1-(tert-butyldimethylsilyloxy)ethyl]-2-azetidinone.

$[\alpha]_D^{25}$+34.2° (C=0.24, CHCl$_3$). IR (Nujol): 3200, 1780, 1740 cm$^{-1}$. NMR (CDCl$_3$, ppm): 0.10 (6H, s), 0.87 (9H, s), 1.23 (3H, d, J=6.3 Hz), 2.13 (3H, s), 3.20 (1H, m), 4.27 (1H, m), 5.90 (1H, m), 6.70 (1H, m).

EXAMPLE 26

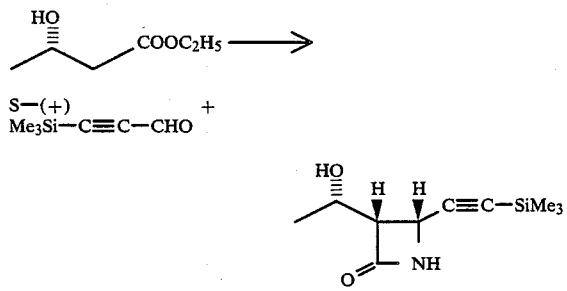

A tetrahydrofuran solution containing trimethylsilylimine compound is obtained from 1,1,1,3,3,3-hexamethyldisilazane (2.7 ml), butyllithium-hexane solution (7.5 ml) and trimethylsilylpropynal (1.5 g) according to a similar manner to that of first half of Example 1. Thus obtained trimethylsilylimine compound is reacted with 1,1,1,3,3,3-hexamethyldisilazane (5 ml), n-butyllithium-hexane solution (13.8 ml) and ethyl (S)-(+)-3-hydroxybutanoate (1.3 g) according to the latter half of Example 1 to give 0.5 g of (3S,4R)-3-[(S)-1-hydroxyethyl]-4-trimethylsilylethynyl-2-azetidinone.

$[\alpha]_D^{25}$+16.7° (C=1.04, EtOH). IR (Nujol): 3360, 3190, 1755 cm$^{-1}$. NMR (CDCl$_3$, ppm): 0.1 (9H, s), 1.37 (3H, d, J=6.9 Hz), 2.87 (1H, m), 3.40 (1H, m), 4.37 (1H, m), 4.43 (1H, d, J=6.0 Hz), 6.43 (1H, m).

EXAMPLE 27

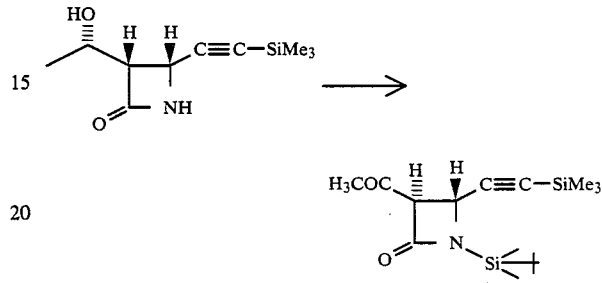

The object compound (0.3 g) of Example 26 is reacted with t-butyldimethylsilyl chloride (0.26 g) and manganese dioxide according to a similar manner to that of Example 24 to give 0.32 g of (3R,4R)-3-acetyl-1-(tert-butyldimethylsilyl)-4-trimethylsilylethynyl-2-azetidinone.

$[\alpha]_D^{25}$−7.2° (C=1.28, CHCl$_3$). IR (Neat): 2170, 1755, 1707 cm$^{-1}$. NMR (CDCl$_3$, ppm): 0.16 (9H, s), 0.33 (6H, s), 1.0 (9H, s), 2.33 (3H, s), 4.33 (1H, d, J=2.7 Hz), 4.57 (1H, d, J=2.7 Hz).

EXAMPLE 28

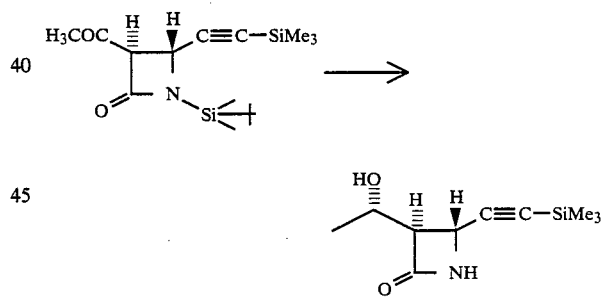

The object compound (0.32 g) of Example 27 is reacted with K-selectride (1 mole solution, 2.4 ml) and then desilylated according to Example 19 to give 0.06 g of (3R,4R)-3-[(S)-1-hydroxyethyl]-4-trimethylsilylethynyl-2-azetidinone.

$[\alpha]_D^{26}$−49.2° (C=1.04, CHCl$_3$). IR (Nujol): 3370, 3200, 1740 cm$^{-1}$. NMR (CDCl$_3$, ppm): 0.10 (9H, s), 1.23 (3H, d, J=6.6 Hz), 2.70 (1H, m), 3.30 (1H, m), 4.13 (1H, m), 4.30 (1H, d, J=2.7 Hz), 6.40 (1H, m).

EXAMPLE 29

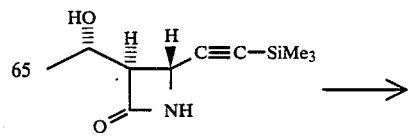

-continued

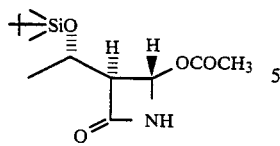

The object compound (0.052 g) of Example 28 is treated according to a similar manner to that of Example 25 to give 0.023 g of (3S,4S)-4-acetoxy-3-[(S)-1-(tert-butyldimethylsilyloxy)ethyl]-2-azetidinone.

$[\alpha]_D^{28}$ −38.7° (C=0.46, CHCl$_3$). IR (Nujol): 3200, 1780, 1740 cm$^{-1}$. NMR (CDCl$_3$, ppm): 0.10 (6H, s), 0.83 (9H, s), 1.23 (3H, d, J=6.3 Hz), 2.07 (3H, s), 3.17 (1H, m), 4.20 (1H, m), 5.83 (1H, m), 6.60 (1H, m).

EXAMPLE 30

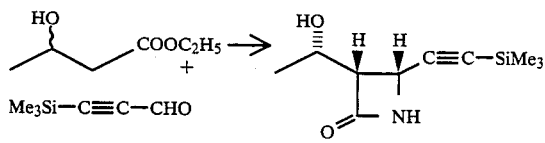

In an argon stream, 1,1,1,3,3,3-hexamethyldisilazane (2.7 ml) is dissolved in dry tetrahydrofuran (10 ml), and a commercial n-butyllithium (1.6M)-hexane solution (7.5 ml) is added dropwise to the solution at −10° C. to −5° C. to produce a solution containing lithium hexamethyldisilazide (LHDS). This solution is stirred at −10° C. for 0.5 hour, and a solution of trimethylsilylpropynal (1.5 g) in dry tetrahydrofuran (3 ml) is added dropwise with maintaining the reaction temperature so as not to exceed −65° C. After completion of the addition, the mixture is stirred at −75° C. for an hour to give a solution containing the corresponding trimethylsilylimine compound.

In an argon stream, 1,1,1,3,3,3-hexamethyldisilazane (5.0 ml) is reacted with a n-butyllithium-hexane solution (13.8 ml) in the same manner as above to give a solution containing LHDS. A solution of ethyl (R,S)-3-hydroxybutanoate (1.3 g) in dry tetrahydrofuran (3 ml) is gradually added dropwise thereto at −65° C. or lower, followed by stirring at −70° C. or lower for an hour. To the mixture is added the above trimethylsilylimine compound-containing solution at −65° C. or lower, and the resulting mixture is stirred at the same temperature for an hour and then at 0° C. for an additional two hours. The mixture is poured into a mixture of ethyl acetate (200 ml), acetic acid (10 ml) and water (200 ml). The organic layer is separated, washed with aqueous sodium bicarbonate. The organic layer is separated, washed with brine, dried over magnesium sulfate and concentrated under reduced pressure. To the residue is added n-hexane (50 ml) and the mixture is allowed to stand at room temperature for one night. The resulting crystals are collected by filtration and dried to give a 1:1 mixture of (1′S, 3S, 4R)- and (1′R, 3R, 4S)-3-(1-hydroxyethyl)-4-trimethylsilylethynyl-2-azetidinone (0.52 g).

IR (Nujol): 3360, 3190, 1755 cm$^{-1}$. NMR (CDCl$_3$, ppm): 0.1 (9H, s), 1.37 (3H, d, J=6.9 Hz), 2.87 (1H, m), 3.40 (1H, m), 4.37 (1H, m), 4.43 (1H, d, J=6.0 Hz), 6.43 (1H, m).

EXAMPLE 31

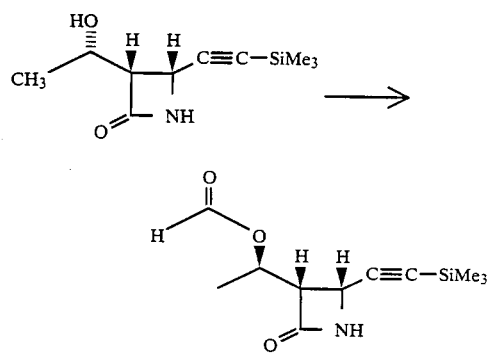

To a stirred solution of a 1:1 mixture of (1′S, 3S, 4R)- and (1′R,3R,4S)-3-(1-hydroxyethyl)-4-trimethylsilylethynyl-2-azetidinone (1.0 g) in dry tetrahydrofuran (THF) (20 ml) is added triphenylphosphine (2.5 g) and formic acid (0.6 ml). After cooling the mixture to 15° C. with stirring, a solution of diethyl azodicarboxylate (1.6 g) in THF (5 ml) is dropwise added thereto during 15 minutes below 25° C. The mixture is stirred for 2 hours at ambient temperature, and then poured into a mixture of ethyl acetate (150 ml) and water (100 ml). The organic layer is separated, washed with brine, dried over magnesium sulfate and filtered. The filtrate is evaporated under reduced pressure followed by subjecting a column chromatography on silica gel (elution by 10% ethyl acetate in hexane) to give a 1:1 mixture of (1′R, 3S, 4R)- and (1′S, 3R, 4S)-3-(1-formyloxyethyl)-4-trimethylsilylethynyl-2-azetidinone (0.78 g).

IR (Nujol): 3250, 2017, 1775, 1760, 1735 cm$^{-1}$. NMR (CDCl$_3$, ppm): 0.13 (9H, s), 1.53 (3H, d, J=6.0 Hz), 3.57 (1H, dd, J=7.5, 5.1 Hz), 4.43 (1H, d, J=5.1 Hz), 5.30 to 5.73 (1H, m), 6.50 (1H, bs), 8.10 (1H, s).

EXAMPLE 32

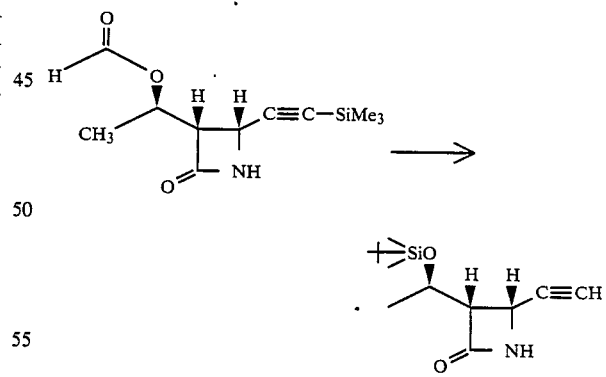

To a stirred solution of the object compound of the Example 31 (1.1 g) in methanol (10 ml) is added 10% hydrochloric acid (2 ml). The mixture is stirred at ambient temperature for 1.5 hours and poured into a mixture of ethyl acetate (100 ml) and saturated sodium bicarbonate aqueous solution (100 ml). The organic layer is separated, washed with brine, dried over magnesium sulfate and evaporated under reduced pressure. Tert-butyldimethylsilyl chloride (1.6 g) and imidazole (1.1 g) are added to a N,N-dimethylformamide (DMF) (10 ml) solution of the above obtained residue at 40° C. followed by stirring at 40° to 45° C. for 2 hours. The mixture is poured into a mixture of ethyl acetate (100 ml) and water (100 ml). The organic layer is separated, washed with water and brine successively, dried over magnesium sulfate and evaporated under reduced pressure. The residue is dissolved in a mixture of THF (10 ml) and methanol (3 ml) followed by treating with cesium fluoride (0.7 g) in water (3 ml) at 65° C. for 1.5 hours. The reaction mixture is diluted with ethyl acetate (100 ml), washed with brine, dried over magnesium sulfate and evaporated under reduced pressure. The residue is subjected to a column chromatography on silica gel (eluent: a mixture of 40% ethyl acetate in hexane) to give a 1:1 mixture of (1′R, 3S, 4R)- and (1′S, 3R, 4S)-3-[1-(tert-butyldimethylsilyloxy)-ethyl]-4-ethynyl-2-azetidinone (1.0 g).

IR (Nujol): 3250, 1755, 1715 cm$^{-1}$. NMR (CDCl$_3$, ppm): 0.10 (6H, s), 0.86 (9H, s), 1.37 (3H, d, J=6 Hz), 2.47 (1H, d, J=1.5 Hz), 3.40 (1H, dd, J=7.0, 5.2 Hz), 4.33 to 4.60 (2H, m), 6.13 (1H, bs).

EXAMPLE 33

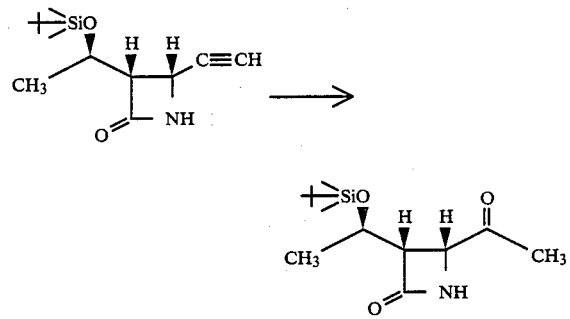

To a stirred solution of the object compound of the Example 3 (1.0 g) in a mixture of methanol (10 ml) and water (2 ml) is added a mixture of mercuric sulfate (0.2 g), ammonium sulfate (0.2 g) and conc. sulfuric acid (trace). The mixture is stirred for 2 hours at ambient temperature, dried over magnesium sulfate and evaporated under reduced pressure. The residue is subjected to a column chromatography on silica gel (eluent: a mixture of 40% ethyl acetate in hexane) to give a 1:1 mixture of (1′R, 3S, 4R)- and (1′S, 3R, 4S)-4-acetyl-3-[1-(tert-butyldimethylsilyloxy)ethyl]-2-azetidinone (0.53 g).

IR (Nujol): 3250, 1780, 1760, 1720, 1690 cm$^{-1}$. NMR (CDCl$_3$, ppm): 0.10 (6H, s), 0.90 (9H, s), 1.33 (3H, d, J=6 Hz), 2.33 (3H, s), 3.60 (1H, dd, J=7.5, 6 Hz), 4.17 to 4.50 (1H, m), 4.26 (1H, d, J=B 6 Hz), 6.83 (1H, bs).

EXAMPLE 34

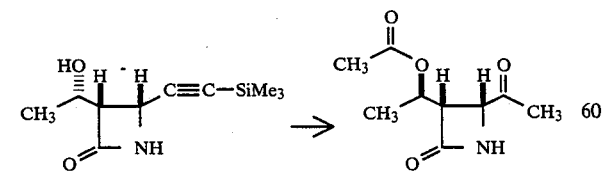

To a stirred solution of a 1:1 mixture of (1′S, 3S, 4R)- and (1′R, 3R, 4S)-3-(1-hydroxyethyl)-4-trimethylsilylethynyl-2-azetidinone (0.5 g) in THF (10 ml) is added triphenylphosphine (1.24 g) and acetic acid (1 ml). A tetrahydrofuran (3 ml) solution containing di-methyl azodicarboxylate (0.76 g) is dropwise added thereto for 15 minutes below 25° C. followed by stirring for 2 hours at ambient temperature. The mixture is diluted with ethyl acetate (100 ml), washed with brine, dried over magnesium sulfate and evaporated under reduced pressure. The residue is subjected to a column chromatography on silica gel (eluent: a mixture of 10% ethyl acetate in hexane) to give a 1:1 mixture of (1′R, 3S, 4R)- and (1′S, 3R, 4S)-3-(1-acetoxyethyl)-4-trimethylsilylethynyl-2-azetidinone. The above obtained compound is dissolved in a mixture of THF (5 ml) and water (1 ml). To the mixture is added mercuric sulfate (0.1 g) and conc. surfuric acid (trace) followed by stirring at 40° C. for 3 hours. The mixture is poured into ethyl acetate (70 ml). The organic layer is separated, washed with brine, dried over magnesium sulfate and evaporated. The residue is subjected to a column chromatography on silica gel (eluent: a mixture of 30% ethyl acetate in hexane) to give a 1:1 mixture of (1′R, 3S, 4R)- and (1′S, 3R, 4S)-3-(1-acetoxyethyl)-4-acetyl-2-azetidinone (0.05 g).

IR (Nujol): 3250, 1780, 1745, 1725, 1710 cm$^{-1}$. NMR (CDCl$_3$, ppm): 1.43 (3H, d, J=6.0 Hz), 2.06 (3H, s), 2.30 (3H, s), 3.83 (1H, dd, J=7.5, 6.0 Hz), 4.50 (1H, d, J=6.0 Hz), 5.00 to 5.37 (1H, m), 6.93 (1H, bs).

EXAMPLE 35

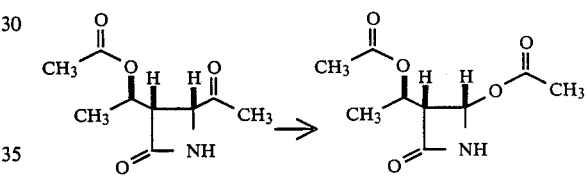

To a stirred solution of the object compound of the Example 34 (0.05 g) in ethyl acetate (5 ml) is added m-chloroperbenzoic acid (0.3 g). The mixture is stirred at 45° C. for 4 hours and poured into a mixture of ethyl acetate (50 ml), saturated sodium bicarbonate aqueous solution (50 ml) and dimethylsulfide (0.3 ml). The organic layer is separated, washed with water and brine successively, dried over magnesium sulfate and evaporated under reduced pressure to give a 1:1 mixture of (1′R, 3R, 4S)- and (1′S, 3S, 4R)-3-(1-acetoxyethyl)-4-acetoxy-2-azetidinone (0.04 g).

IR (CHCl$_3$) 3400, 1780, 1730 cm$^{-1}$. NMR (CDCl$_3$, ppm): 1.43 (3H, d, J=6 Hz), 2.03 (3H, s), 2.10 (3H, s), 3.50 to 3.70 (1H, m), 5.33 to 5.70 (1H, m), 6.03 (1H, d, J=4.8 Hz), 6.90 (1H, bs).

EXAMPLE 36

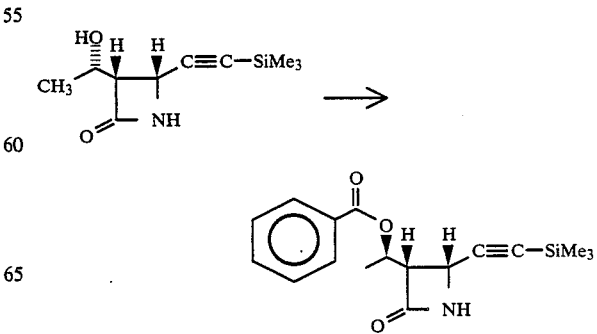

To a stirred solution of (1'S, 3S,4R)-3-(1-hydroxyethyl)-4-trimethylsilylethynyl-2-azetidinone (0.5 g) in THF (10 ml) is added triphenylphosphine (0.9 g) and benzoic acid (0.9 g) below 15° C. A solution of diethyl azodicarboxylate (0.75 g) in THF (5 ml) is dropwise added thereto for 15 minutes below 25° C. followed by stirring for 2.5 hours at the same temperature. The mixture is diluted with ethyl acetate (100 ml), washed with saturated sodium bicarbonate aqueous solution and brine successively, evaporated under reduced pressure. The residual precipitate is extracted with diethyl ether and evaporated under reduced pressure. The residue is subjected to a column chromatography on silica gel (eluent: 10% ethyl acetate in hexane) to give (1'R,3S,4R)-3-(1-benzoyloxyethyl)-4-trimethylsilylethynyl)-2-azetidinone (0.52 g).

$[\alpha]_D^{20}$: −72.5° (C=1.26, CHCl₃). IR (Nujol): 3230, 1765, 1730, 1715 cm⁻¹. NMR (CDCl₃, ppm): −0.04 (9H, s), 1.60 (3H, d, J=6.0 Hz), 3.70 (1H, q, J=6.0 Hz), 4.47 (1H, d, J=5.7 Hz), 5.62 (1H, d,d, J=6.0, 5.7 Hz), 6.93 (1H, s), 7.37 to 7.65 (3H, m), 8.03 to 8.20 (2H, m).

EXAMPLE 37

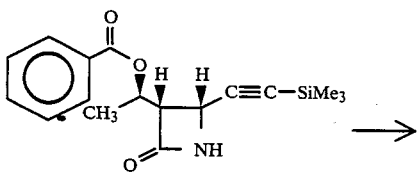

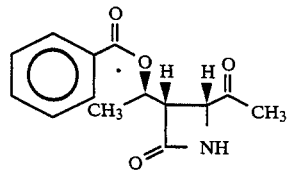

To a stirred solution of the object compound of Example 36 (0.48 g) in a mixture of THF (5 ml) and water (1 ml) is added mercuric sulfate (0.1 g) and conc. sulfuric acid (trace). The mixture is stirred for 3 hours at 60° C. After cooling, the mixture is diluted with ethyl acetate (70 ml), washed with brine, dried over magnesium sulfate and evaporated under reduced pressure. To the residue is added a mixture of hexane (10 ml) and ethyl acetate (2 ml) and allowed to stand at ambient temperature. The resulting crystals are collected by filtration to give (1'R,3S,4R)-4-acetyl-3-(1-benzoyloxyethyl)-2-azetidinone (0.3 g).

$[\alpha]_D^{22}$:−112.9°. IR (Nujol): 3350, 1785, 1170, 1715 cm⁻¹.

NMR (CDCl₃, ppm): 1.53 (3H, d, J=6.9 Hz), 2.13 (3H, s), 3.93 (1H, dd, J=6.9, 6.0 Hz), 4.48 (1H, d, J=6 Hz), 5.07 to 5.50 (1H, m), 6.80 (1H, s), 7.27 to 7.63 (3H, m), 7.85 to 8.10 (2H, m).

EXAMPLE 38

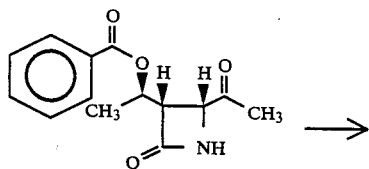

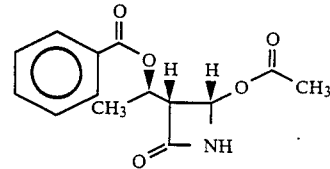

To a stirred solution of the object compound of Example 37 (0.12 g) in ethyl acetate (5 ml) is added m-chloroperbenzoic acid (0.4 g). The mixture is stirred for 5 hours at 55° to 60° C. and then poured into a mixture of ethyl acetate (50 ml), saturated sodium bicarbonate aqueous solution (30 ml) and dimethylsulfide (0.17 ml). The organic layer is separated, washed with water and brine successively, dried over magnesium sulfate and evaporated under reduced pressure. The residue is subjected to a column chromatography on silica gel (eluent: 15% ethyl acetate in hexane) to give 0.12 g of (1'R,3R,4S)-4-acetoxy-3-(1-benzoyloxyethyl)-2-azetidinone.

$[\alpha]_D^{20}$: −124.9°. IR (Nujol): 3240, 1780, 1735, 1715 cm⁻¹. NMR (CDCl₃, ppm): 1.57 (3H, d, J=6.3 Hz), 1.90 (3H, s), 3.72 (1H, q, d, J=2.1, 9.0 Hz), 3.60–3.83 (1H, m), 6.03 (1H, d, J=5.4 Hz), 7.10 (1H, s), 7.38–7.67 (3H, m), 7.96–8.17 (2H, m).

EXAMPLE 39

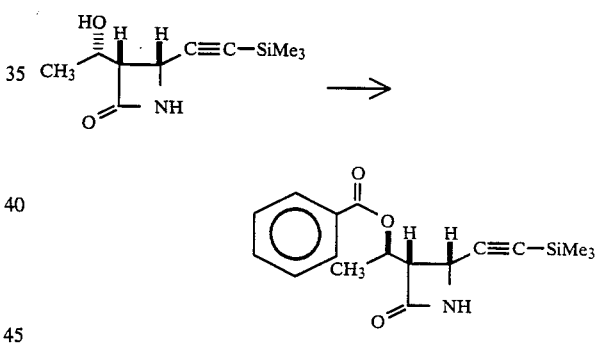

In a similar manner to that of Example 36, a 1:1 mixture of (1'S,3R,4S)- and (1'R,3S,4R)-3-(1-benzoyloxyethyl)-4-trimethylsilylethynyl-2-azetidinone (2.5 g) is obtained from a 1:1 mixture of (1'S,3S,4R)- and (1'R,3R,4S)-3-(1-hydroxyethyl)-4-trimethylsilylethynyl-2-azetidinone (2.0 g).

IR (Nujol): 3230, 1765, 1730, 1715 cm⁻¹. NMR (CDCl₃, ppm): −0.04 (9H, s), 1.60 (3H, d, J=6.0 Hz), 3.70 (1H, q, J=6.0 Hz), 4.47 (1H, d, J=5.7 Hz), 5.62 (1H, d,d, J=6.0, 5.7 Hz), 6.93 (1H, s), 7.37 to 7.65 (3H, m), 8.03 to 8.20 (2H, m).

EXAMPLE 40

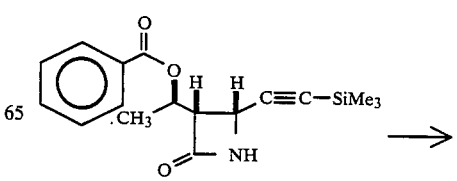

-continued

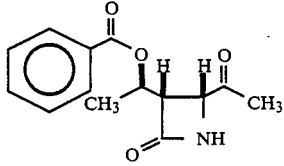

In a similar manner to that of Example 37, a 1:1 mixture of (1′R,3S,4R)- and (1′S,3R,4S)-4-acetyl-3-(1-benzoyloxyethyl)-2-azetidinone (1.62 g) is obtained from the object compound of Example 39 (1.7 g).

IR (Nujol): 3350, 1785, 1770, 1715 cm⁻¹. NMR (CDCl₃, ppm): 1.53 (3H, d, J=6.9 Hz), 2.13 (3H, s), 3.93 (1H, dd, J=6.9, 6.0 Hz), 4.48 (1H, d, J=6 Hz), 5.07 to 5.50 (1H, m), 6.80 (1H, s), 7.27 to 7.63 (3H, m), 7.85 to 8.10 (2H, m).

EXAMPLE 41

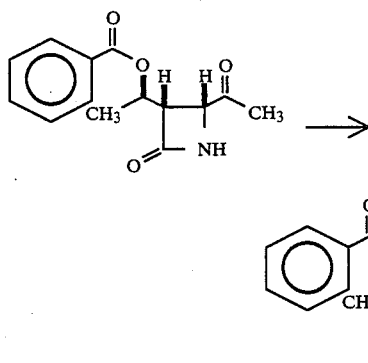

In a similar manner to that of Example 38, a 1:1 mixture of (1′R,3R,4S)- and (1′S,3S,4R)-4-acetoxy-3-(1-benzoyloxyethyl)-2-azetidinone (1.62 g) is obtained from the object compound of Example 40 (1.7 g).

IR (Nujol): 3240, 1780, 1735, 1715 cm⁻¹. NMR (CDCl₃, ppm): 1.57 (3H, d, J=6.3 Hz), 1.90 (3H, s), 3.72 (1H, q, d, J=2.1, 9.0 Hz), 3.60–3.83 (1H, m), 6.03 (1H, d, J=5.4 Hz), 7.10 (1H, s), 7.38–7.67 (3H, m), 7.96–8.17 (2H, m).

EXAMPLE 42

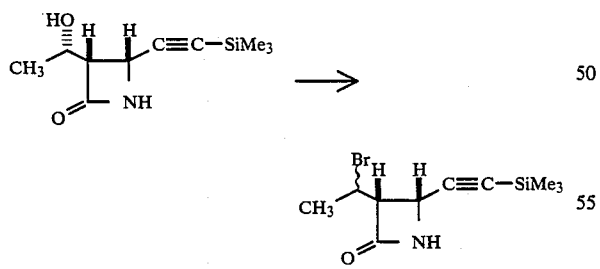

To a stirred solution of carbon tetrabromide (1.2 g) in THF (20 ml) is added triphenylphosphine (1.0 g) at 5° C. After the stirring is continued for 20 minutes at the same temperature, a 1:1 mixture of (1′S,3S,4R)- and (1′R,3R,4S)-3-(1-hydroxyethyl)-4-trimethylsilylethynyl-2-azetidinone (0.5 g) is added thereto. The mixture is stirred for 2 hours at ambient temperature followed by filtration. The filtrate is evaporated under reduced pressure to give a residue. The residue is subjected to a column chromatography on silica gel (eluent: 10% ethyl acetate in hexane) to give a 1:1 mixture of (3R,4R)- and (3S,4S)-3-(1-bromoethyl)-4-trimethylsilylethynyl-2-azetidinone (0.45 g).

IR (Nujol): 3150, 3050, 1755 cm⁻¹. NMR (CDCl₃, ppm): 0.20 (9H, s), 2.00 (3H, d, J=6.3 Hz), 3.77 (1H, dd, J=5.0, 11.0 Hz), 4.33 to 4.73 (1H, m), 4.46 (1H, d, J=5 Hz), 6.33 (1H, bs).

EXAMPLE 43

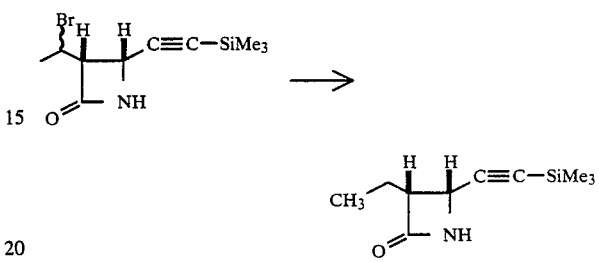

To a stirred solution of the object compound of the Example 14 (0.6 g) in a mixture of N,N-dimethylformamide (10 ml) and formic acid (3 ml) is added Zinc powder (0.5 g) at 10° C. The solution is stirred for 2 hours at ambient temperatures and then diluted with ethyl acetate (150 ml). The solution is washed with brine, dried over magnesium sulfate and evaporated. The residue is subjected to a column chromatography on silica gel (eluent: 13% ethyl acetate in hexane) to give a 1:1 mixture of (3R,4R)- and (3S,4S)-3-ethyl-4-trimethylsilylethynyl-2-azetidinone (0.26 g).

IR (Nujol): 3200, 2150, 1755, 1700 cm⁻¹. NMR (CDCl₃, ppm): 0.17 (9H, s), 1.10 (3H, t, J=6.5 Hz), 1.67 to 2.10 (2H, m), 3.10 to 3.43 (1H, m), 4.37 (1H, d, J=6.0 Hz), 6.20 (1H, bs).

EXAMPLE 44

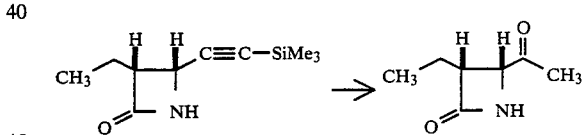

In a similar manner to that of Example 37, a 1:1 mixture of→(3R,4R)- and (3S,4S)-4-acetyl-3-ethyl-2-azetidinone (0.06 g) is obtained from the object compound of Example 43 (0.1 g).

IR (Nujol): 3260, 1780, 1710, 1705 cm⁻¹. NMR (CDCl₃, ppm): 1.10 (3H, t, J=6.0 Hz), 1.33 to 1.83 (2H, m), 2.27 (3H, s), 3.33 to 3.73 (1H, m), 4.40 (1H, d, J=6.0 Hz), 7.00 (1H, bs).

EXAMPLE 45

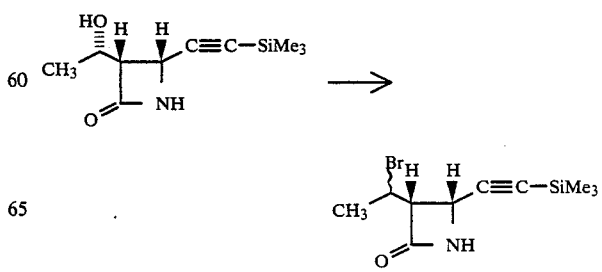

In a similar manner to that of Example 42, (3R,4R)-3-(1-bromoethyl)-4-trimethylsilylethynyl-2-azetidinone (0.46 g) is obtained from (1'S,3S,4R)-3-(1-hydroxyethyl)-4-trimethylsilylethynyl-2-azetidinone (0.50 g).

$[\alpha]_D^{20}$: −232.9° (C=1.14CHCl$_3$). IR (Nujol): 3150, 3050, 1755 cm$^{-1}$. NMR (CDCl$_3$, ppm): 0.20 (9H, s), 2.00 (3H, d, J=6.3 Hz), 3.77 (1H, dd, J=5.0, 11.0 Hz), 4.33 to 4.73 (1H, m), 4.46 (1H, d, J=5 Hz), 6.33 (1H, bs).

EXAMPLE 46

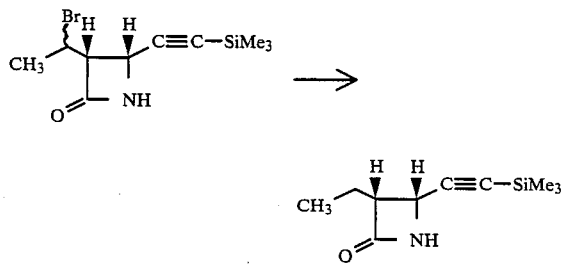

In a similar manner to that of Example 43, (3R,4R)-3-ethyl-4-trimethylsilylethynyl-2-azetidinone (0.2 g) is obtained from the object compound of Example 45 (0.46 g).

$[\alpha]_D^{20}$: −41.1° (C=1.08, CHCl$_3$). IR (Nujol): 3200, 2150, 1755, 1700 cm$^{-1}$. NMR (CDCl$_3$, ppm): 0.17 (9H, s), 1.10 (3H, t, J=6.5 Hz), 1.67 to 2.10 (2H, m), 3.10 to 3.43 (1H, m), 4.37 (1H, d, J=6.0 Hz), 6.20 (1H, bs).

EXAMPLE 47

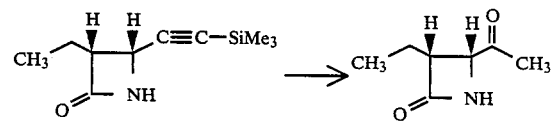

In a similar manner to that of Example 37, (3R,4R)-3-ethyl-4-trimethylsilylethynyl-2-azetidinone (0.18 g) is reacted with mercuric sulfate (0.05 g) and concentrated sulfuric acid (trace). To the reaction mixture is added sodium bicarbonate (0.1 g) and then evaporated under reduced pressure. The residue is extracted with a mixture of ethyl acetate (30 ml) and THF (30 ml), and then evaporated under reduced pressure. The residue is subjected to a column chromatography on silica gel (eluent: 50% ethyl acetate in hexane) to give (3R,4R)-4-acetyl-3-ethyl-2-azetidinone (0.08 g).

$[\alpha]_D^{20}$: +80.0° (C=1.52, CHCl$_3$). IR (Nujol): 3260, 1780, 1710, 1705 cm$^{-1}$. NMR (CDCl$_3$, ppm): 1.10 (3H, t, J=6.0 Hz), 1.33 to 1.83 (2H, m), 2.27 (3H, s), 3.33 to 3.73 (1H, m), 4.40 (1H, d, J=6.0 Hz), 7.00 (1H, bs).

EXAMPLE 48

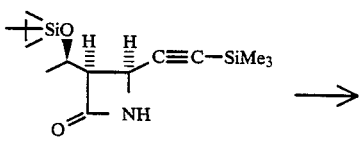

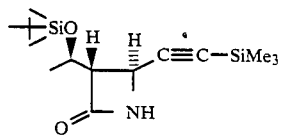

To a solution of (3R,4S)-3-[(R)-1-(tert-butyldimethylsilyloxy)ethyl]-4-trimethylsilylethynyl-2-azetidinone (0.73 g) in dichloromethane (10 ml) was added triethylamine (1 ml). To the solution, trimethylsilyl trifluoromethanesulfonate (1.2 ml) was added at 5° C. and the mixture was stirred for 15 hours at ambient temperature. The reaction mixture was poured into a mixture of ethyl acetate (100 ml), 10% hydrochloric acid (10 ml) and water (100 ml). After stirring for 30 minutes at ambient temp., the organic layer was separated, washed successively with brine, aqueous solution of sodium bicarbonate and brine, dried over magnesium sulfate and concentrated under reduced pressure. The residue was recrystallized from n-hexane to give 0.64 g of (3S,4S)-3-[(R)-1-(tert-butyldimethylsilyloxy)ethyl]-4-trimethylsilylethynyl-2-azetidinone.

$[\alpha]_D^{21}$: +39.0 (C=1.016, CHCl$_3$). IR (Nujol): 3170, 2200, 1770, 1720. NMR (CDCl$_3$, ppm): 0.13 (6H, s), 0.20 (9H, s), 0.87 (9H, s), 1.23 (3H, d, J=7.2 Hz), 3.17–3.30 (1H, m), 4.23–4.37 (1H, m), 4.30 (1H, d, J=2.7 Hz), 6.17 (1H, br s).

EXAMPLE 49

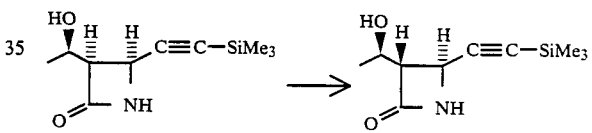

Trimethylsilyl trifluoromethanesulfonate (0.48 ml) was added to a mixture of (3R,4S)-3-[(R)-1-hydroxyethyl]-4-trimethylsilylethynyl-2-azetidinone (0.15 g), triethylamine (0.4 ml) and dichloromethane (7 ml) at 5° C. The mixture was stirred at ambient temperature for 3 hours and poured into a mixture of ethyl acetate (70 ml), ethanol (10 ml), 10% hydrochloric acid (10 ml) and water (50 ml). After stirring for 30 min. at ambient temp., the organic layer was separated, washed successively with brine, saturated aqueous sodium bicarbonate and brine, dried over magnesium sulfate and concentrated under reduced pressure. The precipitates were recrystallized from n-hexane to give 0.13 g of (3S,4S)-3-[(R)-1-hydroxyethyl]-4-trimethylsilylethynyl-2-azetidinone.

$[\alpha]_D^{23}$: +65.14. IR (Nujol): 3370, 3200, 1740 cm$^{-1}$. NMR (CDCl$_3$, ppm): 0.10 (9H, s), 1.30 (3H, d, J=6.6 Hz), 2.90 (1H, m), 3.33 (1H, m), 4.20 (1H, m), 4.30 (1H, d, J=2.7 Hz), 6.50 (1H, m).

EXAMPLE 50

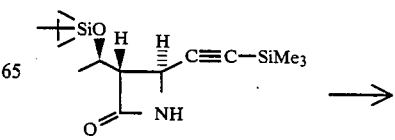

-continued

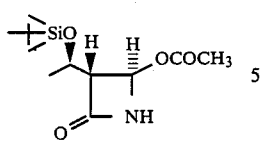

The object compound (0.3 g) of Example 48 was dissolved in a mixture of tetrahydrofuran (5 ml) and water (0.5 ml), and stirred at 25° C. for 4 hours in the presence of catalytic amount of murcuric sulfate and sulfuric acid. The reaction mixture was poured into a mixture of ethyl acetate (50 ml) and water (50 ml). The organic layer was separated, washed with brine, dried over magnesium sulfate and concentrated under reduced pressure. Thus obtained residue was dissolved in ethyl acetate (10 ml). To the solution, m-chloroperbenzoic acid (1.0 g) was added and the mixture was stirred at room temperature for 3 hours. The mixture was poured into a mixture of ethyl acetate (100 ml), saturated aqueous sodium bicarbonate (30 ml) and dimethyl sulfide (0.4 ml) followed by stirring for 1 hour at ambient temperature. The organic layer was separated, washed with brine, dried over magnesium sulfate and concentrated under reduced pressure. The residue was subjected to silica gel column chromatography (eluent: 15% ethyl acetate-85% n-hexane) to give 0.14 g of (3R,4R)-4-acetoxy-3-[(R)-1-(tert-butyldimethylsilyloxy)ethyl]-2-azetidinone.

$[\alpha]_D^{24}$: +54.7° (C=1.036, CHCl$_3$). IR (Nujol): 3200, 1780, 1740. NMR (CDCl$_3$, ppm): 0.10 (6H, s), 0.87 (9H, s), 1.23 (3H, d, J=6.3 Hz), 2.13 (3H, s), 3.20 (1H, m), 4.27 (1H, m), 5.90 (1H, m), 6.70 (1H, br. s).

What is claimed is:

1. A method of producing an azetidinone derivative of the formula:

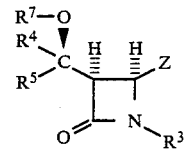

wherein, Z is selected from the group consisting of alkanoyl, alkenyl, alkynyl and alkynyl substituted with trialkylsilyl,
$R^3$ is a hydrogen or a protective group,
$R^4$ and $R^5$, which may be the same or different, are hydrogen or lower alkyl group,
$R^7$ is a hydrogen or a protective group,
⊪ is an alpha configuration bond and
▶ is a beta configuration bond, which comprises reacting a compound of the formula:

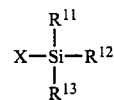

wherein Z, $R^3$, $R^4$, $R^5$, $R^7$, and are each as defined above, with a compound of the formula $$\begin{array}{c} R^{11} \\ | \\ X-Si-R^{12} \\ | \\ R^{13} \end{array}$$

wherein $R^{11}$, $R^{12}$ and $R^{13}$, which may be the same or different, are hydrocarbon residue, and
X is a strong acid residue, and then subjecting the resulting compound to hydrolysis.

* * * * *